(12) United States Patent
Kordis et al.

(10) Patent No.: US 6,360,128 B2
(45) Date of Patent: *Mar. 19, 2002

(54) CARDIAC MAPPING AND ABLATION SYSTEMS

(75) Inventors: Thomas F. Kordis, Sunnyvale; David K. Swanson, Mountain View, both of CA (US)

(73) Assignee: EP Technologies, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/747,294

(22) Filed: Dec. 21, 2000

Related U.S. Application Data

(60) Continuation of application No. 08/934,577, filed on Sep. 22, 1997, now Pat. No. 6,233,491, which is a continuation of application No. 08/574,995, filed on Dec. 19, 1995, now abandoned, which is a division of application No. 08/136,218, filed on Oct. 14, 1993, now Pat. No. 5,476,495, which is a division of application No. 08/033,681, filed on Mar. 16, 1993, now abandoned.

(51) Int. Cl.[7] ................................................. A61N 1/00
(52) U.S. Cl. ........................ 607/122; 600/374; 128/898
(58) Field of Search ................................. 607/115, 116, 607/119, 126, 122, 123; 600/373–375, 381; 606/41, 47; 128/898

(56) References Cited

U.S. PATENT DOCUMENTS

| | | |
|---|---|---|
| 4,522,212 A | 6/1985 | Gelinas et al. |
| 4,641,649 A | 2/1987 | Walinsky et al. |
| 4,660,571 A | 4/1987 | Hess et al. |
| 4,699,147 A | 10/1987 | Chilson et al. |
| 4,758,222 A | 7/1988 | McCoy |
| 4,785,815 A | 11/1988 | Cohen |
| 4,808,164 A | 2/1989 | Hess |
| 4,832,048 A | 5/1989 | Cohen |
| 4,892,102 A | 1/1990 | Astrinsky |
| 4,922,912 A | 5/1990 | Watanabe |
| 4,928,689 A | 5/1990 | Hauser |
| 4,940,064 A | 7/1990 | Desai |
| 4,955,382 A | 9/1990 | Franz et al. |
| 4,979,510 A | 12/1990 | Franz et al. |
| 4,998,916 A | 3/1991 | Hammerslag et al. |
| 5,010,894 A | 4/1991 | Edhag |
| 5,156,151 A | 10/1992 | Imran |
| 5,230,349 A | 7/1993 | Langberg |
| 5,237,996 A | 8/1993 | Waldman et al. |
| 5,324,284 A | 6/1994 | Imran |
| 5,409,000 A | 4/1995 | Imran |
| 5,415,166 A | 5/1995 | Imran |
| 5,465,717 A | 11/1995 | Imran et al. |
| 5,476,495 A | 12/1995 | Kordis et al. |

*Primary Examiner*—Jeffrey R. Jastrzab
(74) *Attorney, Agent, or Firm*—Lyon & Lyon LLP

(57) ABSTRACT

A probe for cardiac diagnosis and/or treatment has a catheter tube. The distal end of the catheter tube carries first and second electrode elements. The probe includes a mechanism for steering the first electrode element relative to the second electrode element in multiple directions.

10 Claims, 18 Drawing Sheets

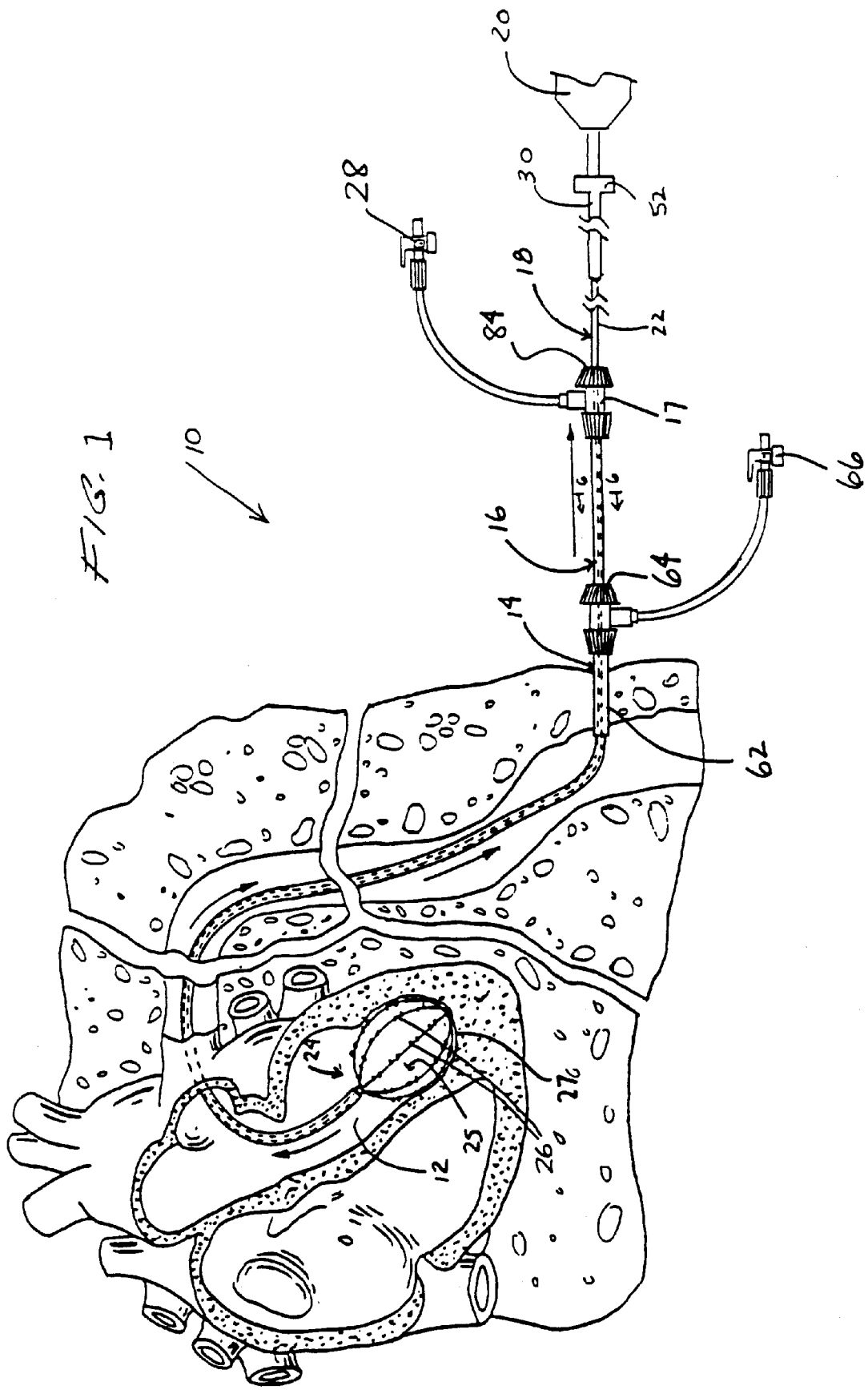

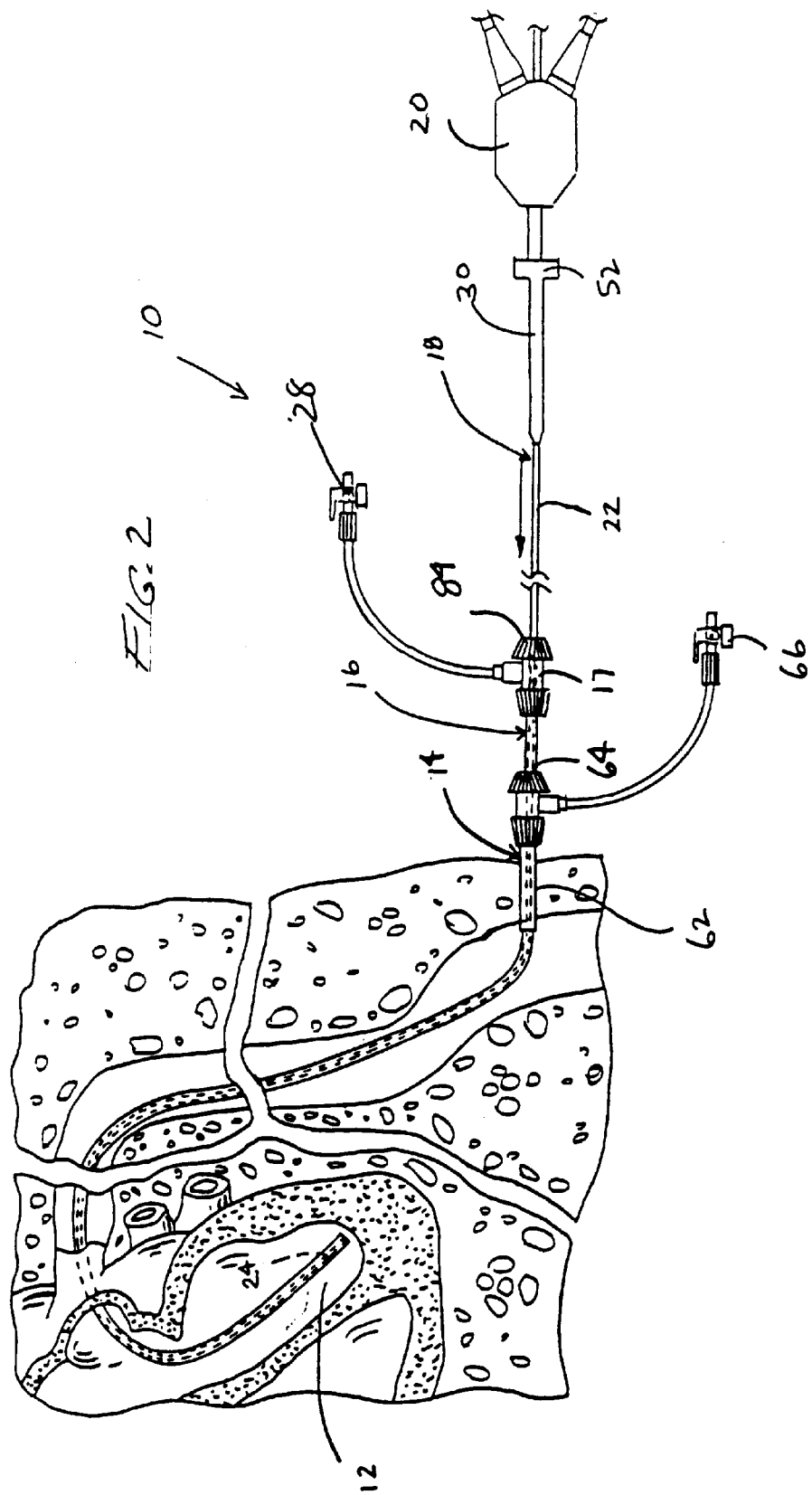

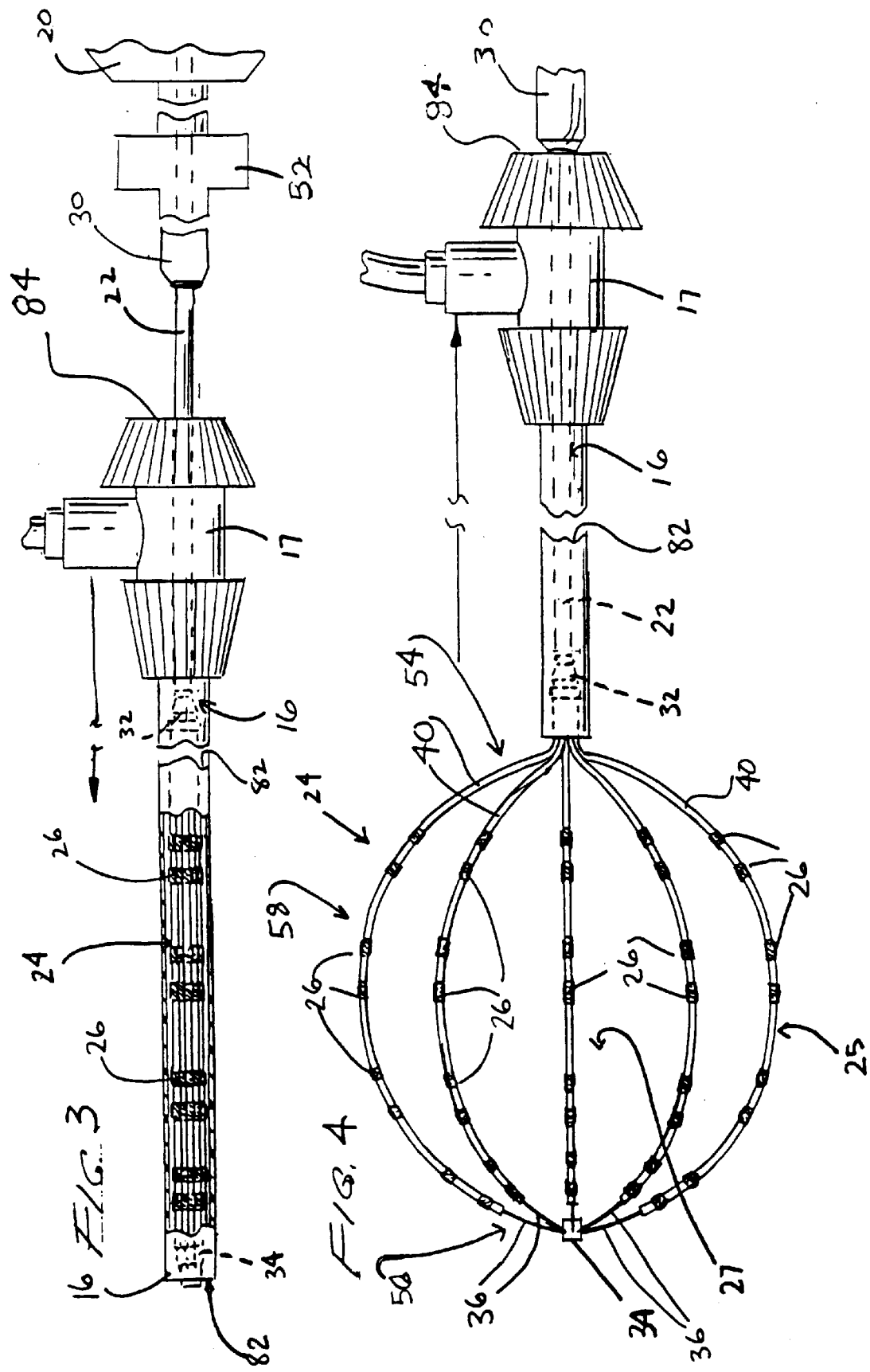

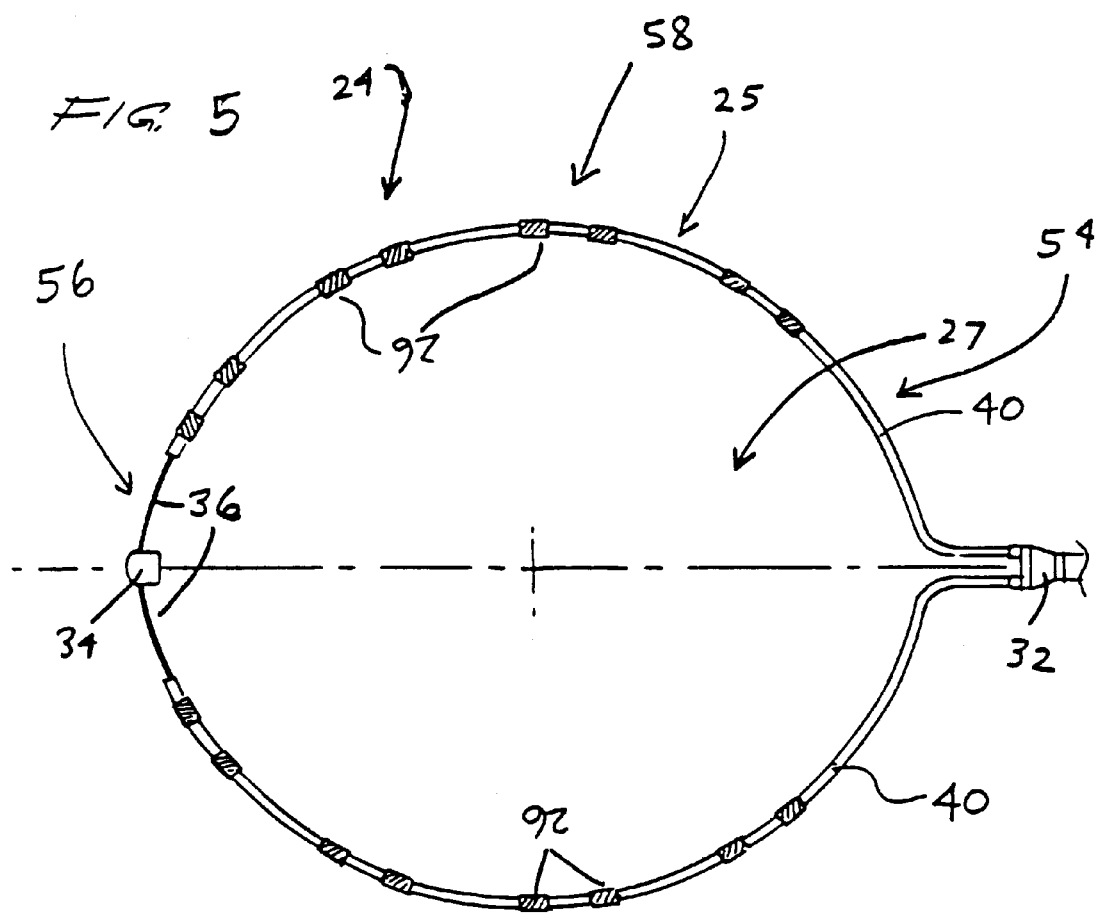
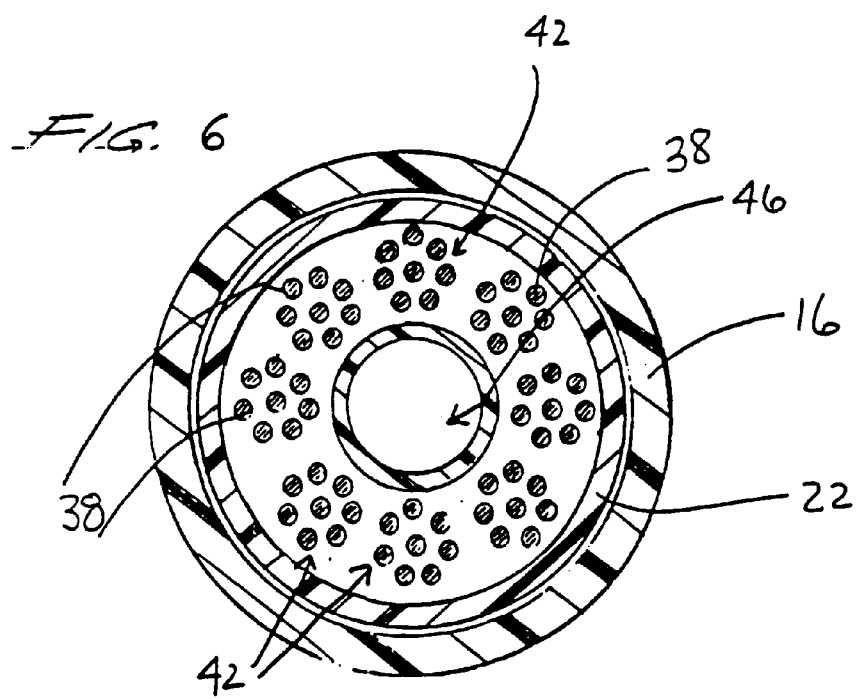

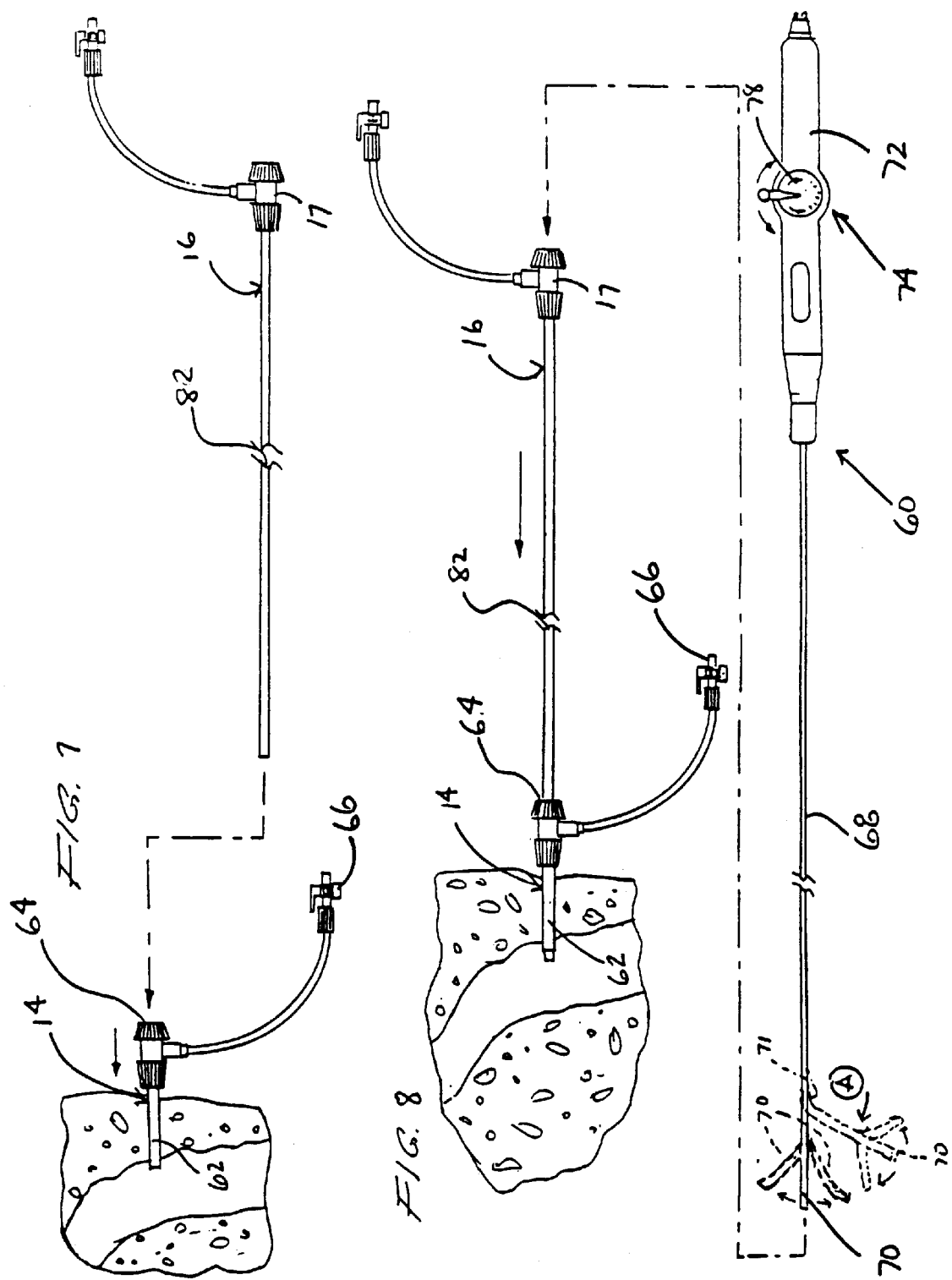

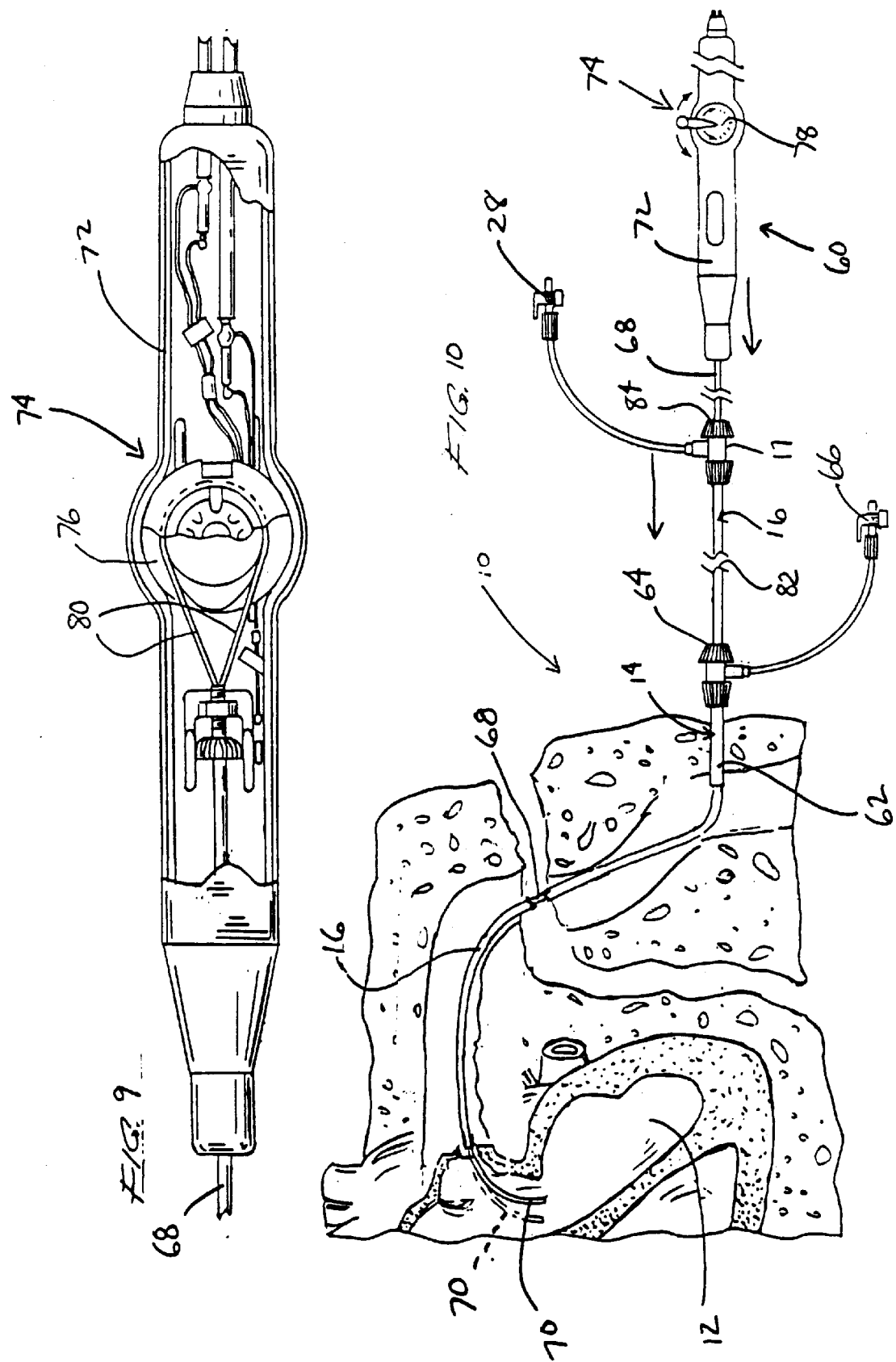

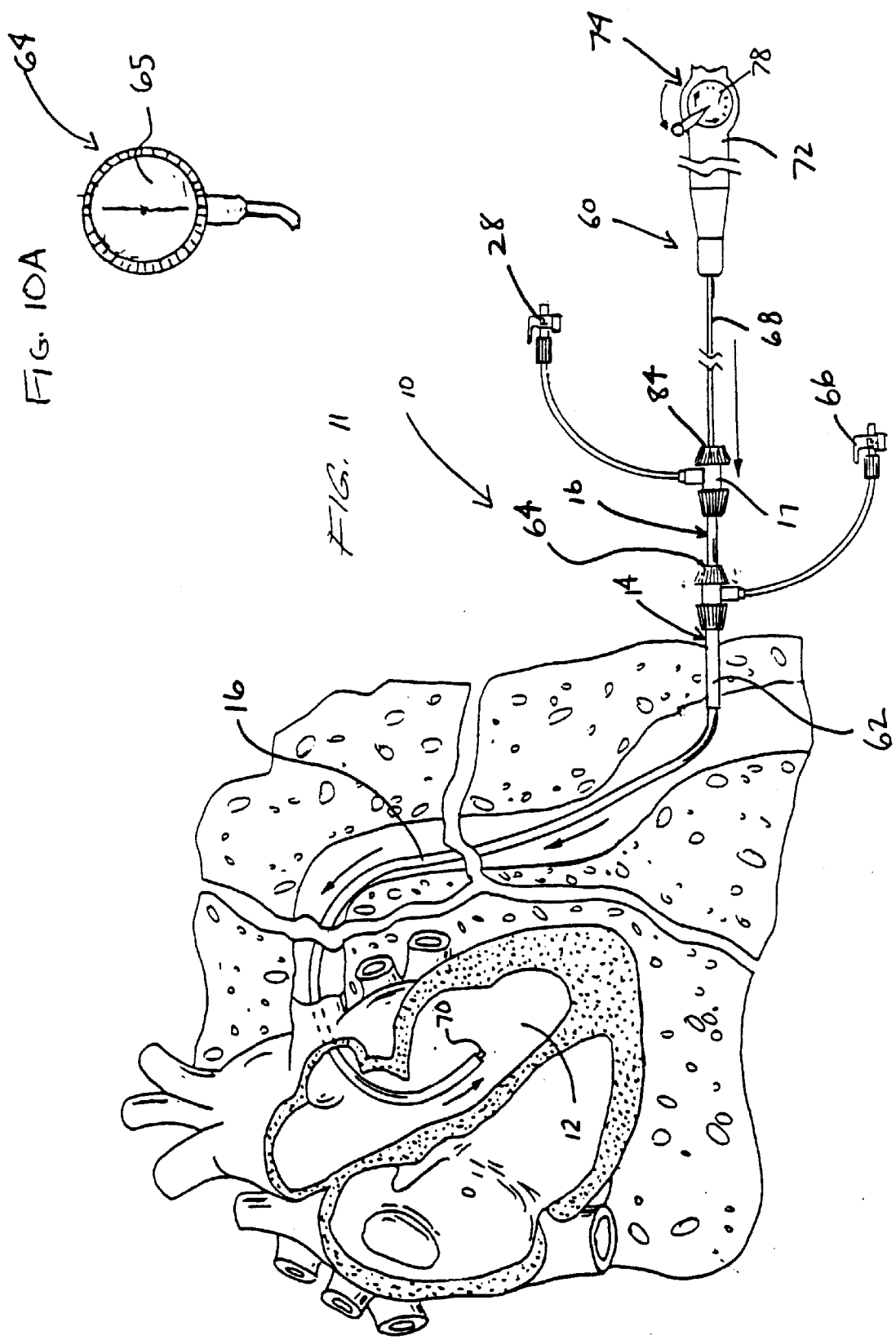

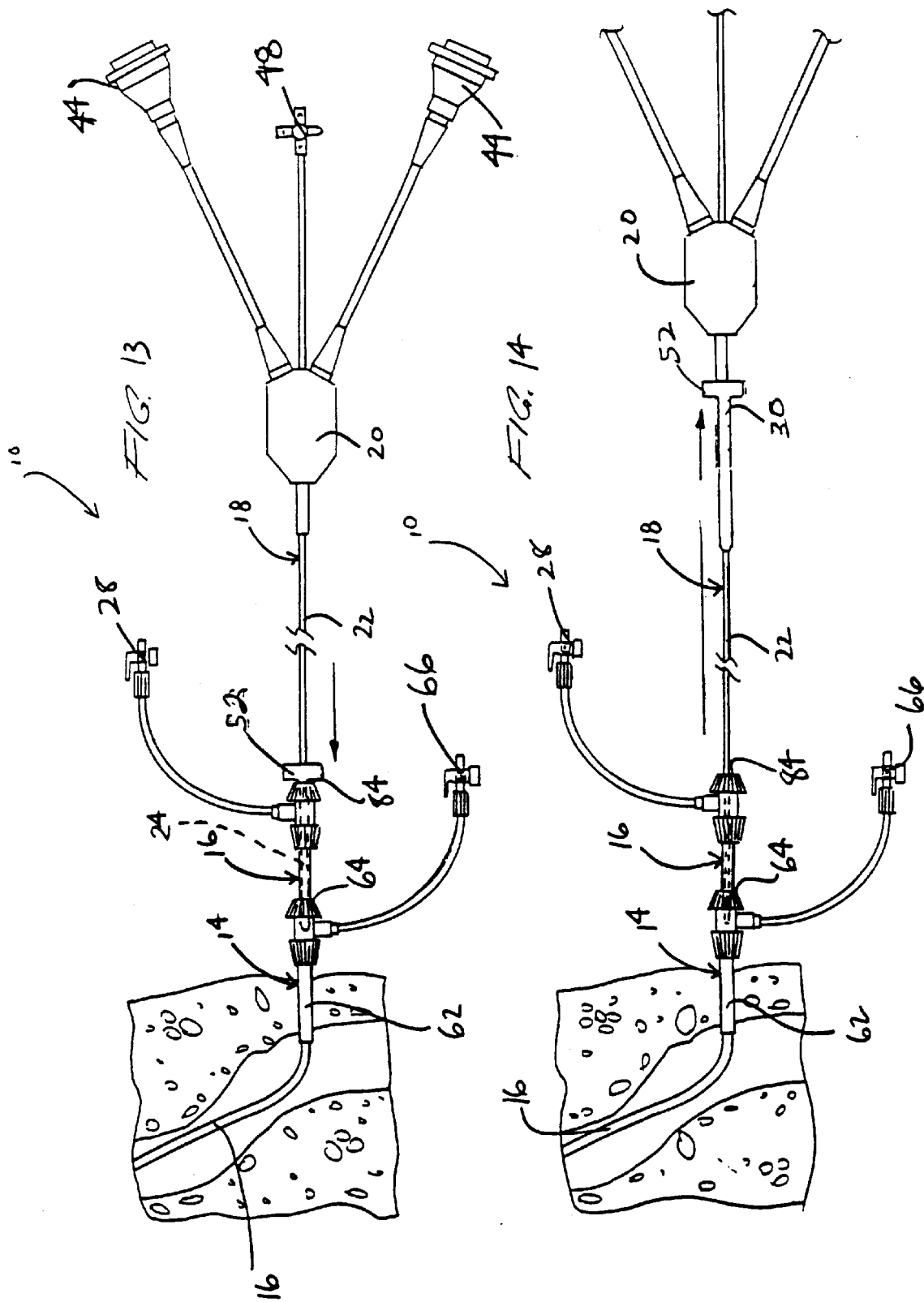

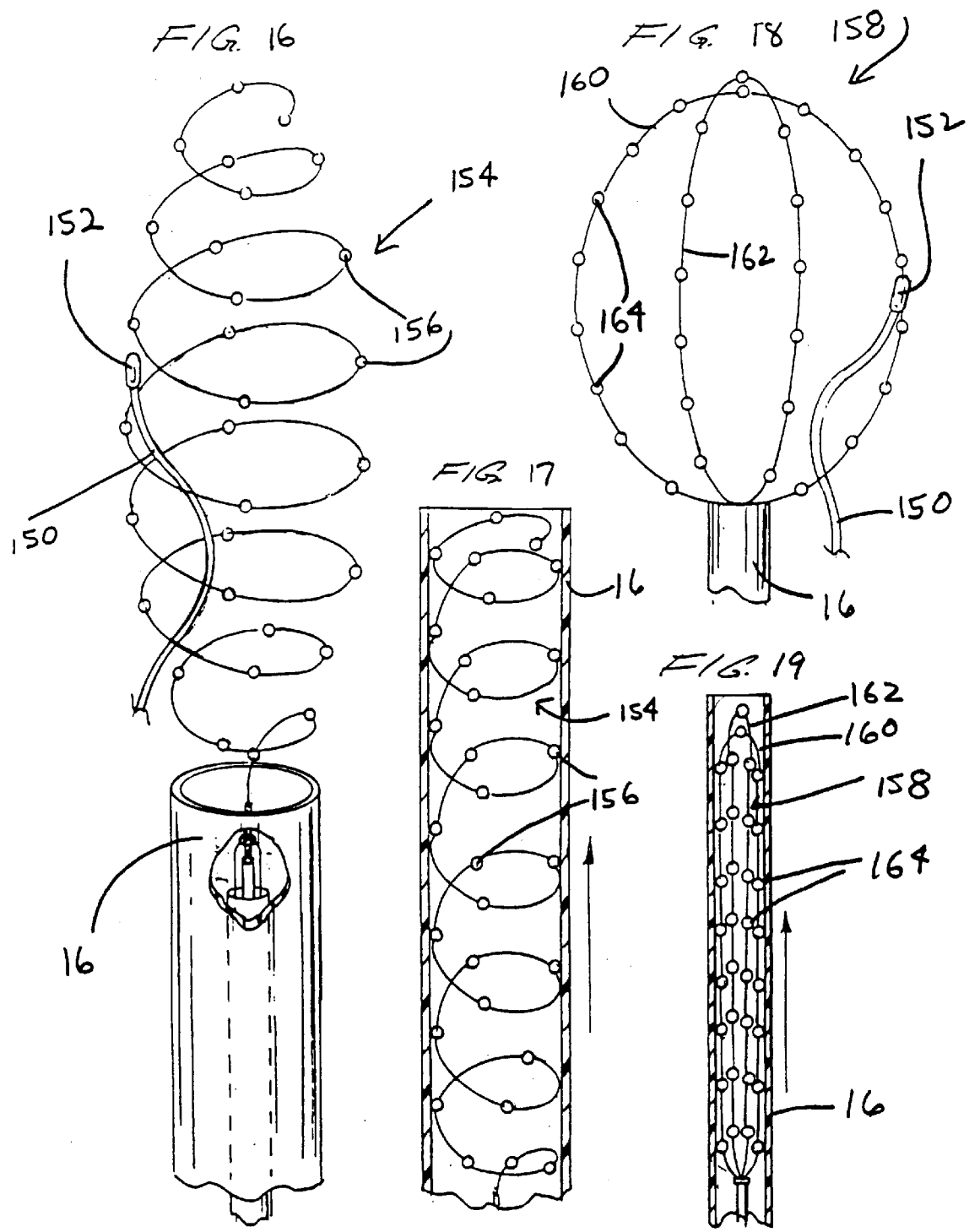

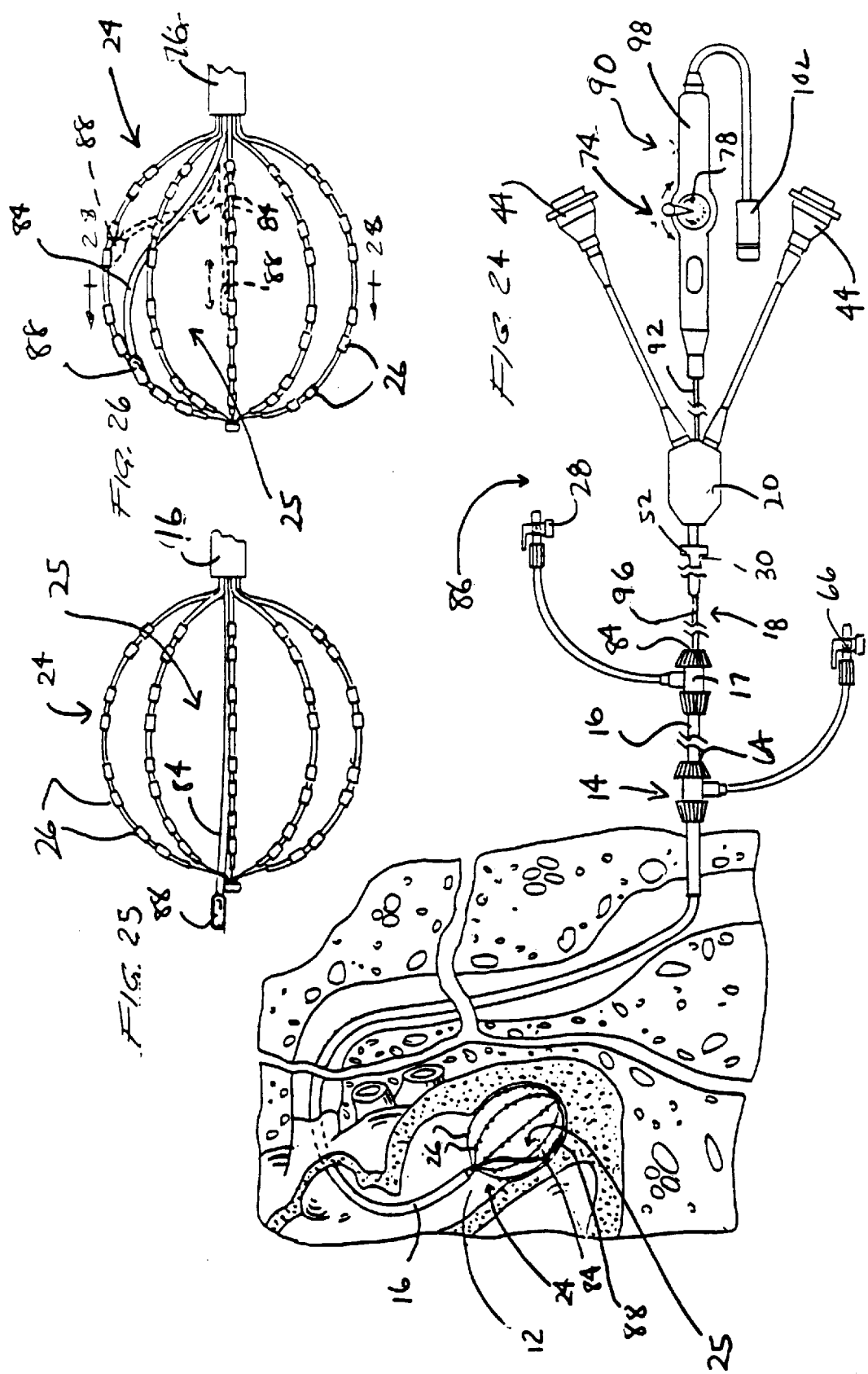

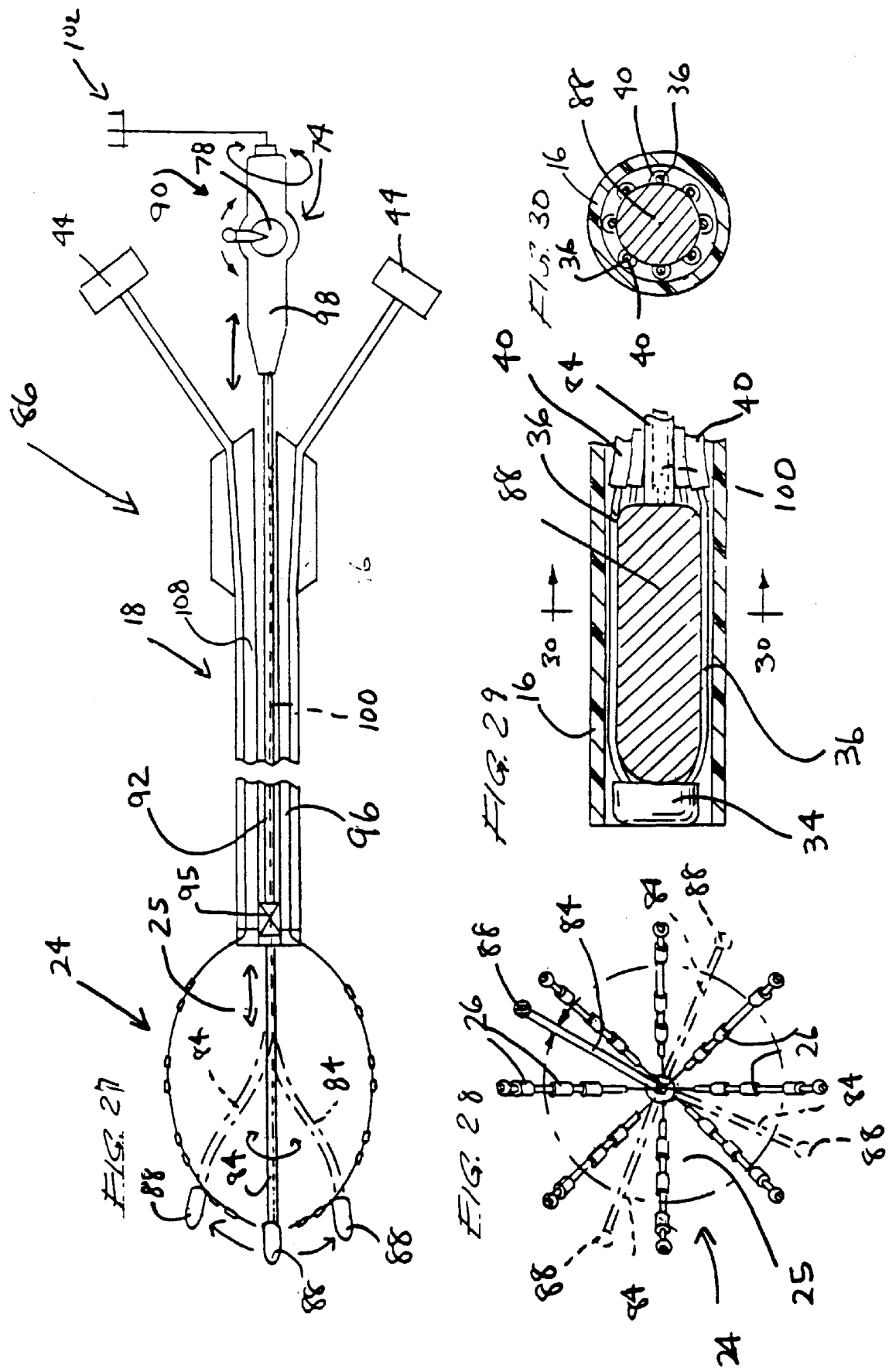

CARDIAC MAPPING AND ABLATION SYSTEMS

This is a continuation of application Ser. No. 08/934,577, filed Sep. 22, 1997 now U.S. Pat. No. 6,233,491, which is a continuation of application Ser. No. 08/574,995, filed Dec. 19, 1995, now abandoned, which is a divisional of application Ser. No. 08/136,218, filed Oct. 14, 1993, now U.S. Pat. No. 5,476,495, which is a divisional of application Ser. No. 08/033,681, filed Mar. 16, 1993, now abandoned.

FIELD OF THE INVENTION

The invention relates to systems and methods for mapping and ablating the interior regions of the heart for treatment of cardiac conditions.

BACKGROUND OF THE INVENTION

Physicians make use of catheters today in medical procedures to gain access into interior regions of the body to ablate targeted tissue areas. It is important for the physician to be able to carefully and precisely control the position of the catheter and its emission of energy within the body during tissue ablation procedures.

The need for careful and precise control over the catheter is especially critical during procedures that ablate tissue within the heart. These procedures, called electrophysiological therapy, are becoming more widespread for treating cardiac rhythm disturbances.

During these procedures, a physician steers a catheter through a main vein or artery into the interior region of the heart that is to be treated. The physician then further manipulates a steering mechanism to place the electrode carried on the distal tip of the catheter into direct contact with the tissue that is to be ablated. The physician directs energy from the electrode through-tissue to an indifferent electrode (in a uni-polar electrode arrangement) or to an adjacent electrode (in a bi-polar electrode arrangement) to ablate the tissue and form a lesion.

Cardiac mapping can be used before ablation to locate aberrant conductive pathways within the heart. The aberrant conductive pathways constitute peculiar and life threatening patterns, called dysrhythmias. Mapping identifies regions along these pathways, called foci, which are then ablated to treat the dysrhythmia.

There is a need for cardiac mapping and ablation systems and procedures that can be easily deployed with a minimum of manipulation and effort.

There is also a need for systems and procedures that are capable of performing cardiac mapping in tandem with cardiac ablation. Such multipurpose systems must also be easily. introduced into the heart. Once deployed, such multipurpose systems also must be capable of mapping and ablating with a minimum of manipulation and effort.

SUMMARY OF THE INVENTION

A principal objective of the invention is to provide improved probes to carry out cardiac mapping and/or cardiac ablation procedures quickly and accurately.

Another principal objective of the invention is to provide improved probes that integrate mapping and ablation functions.

The invention provides a probe for use within the heart to contact endocardial tissue. The probe includes a catheter tube having a distal end that carries a first electrode element.

The probe also includes a second electrode element on the distal end. The second electrode element defines a three-dimensional structure that extends along an axis and that has an open interior. The probe includes a mechanism for moving the first electrode element within the open interior of the second electrode element in a first direction along the axis of the second electrode element, in a second direction rotating about the axis of the second electrode element, and in a third direction normal to the axis of the second electrode element.

In a preferred embodiment, the movable first electrode element serves to ablate myocardial tissue. The second electrode element independently serves to sense electrical activity in endocardial tissue.

Other features and advantages of the inventions are set forth in the following Description and Drawings, as well as in the appended Claims.

BRIEF DESCRIPTION OF THE DRAWINGS

FIG. 1 is a side view, with portions fragmented and in section, of an endocardial mapping system that embodies the features of the invention, shown deployed and ready for use inside a heart chamber;

FIG. 2 is a side view of endocardial mapping system shown in FIG. 1, with portions fragmented and in section, showing the electrode-carrying basket in a collapsed condition before deployment inside the heart chamber;

FIG. 3 is an enlarged side view of the electrode-carrying basket and movable guide sheath shown in FIG. 2, with portions fragmented and in section, showing the electrode-carrying basket in a collapsed condition before deployment;

FIG. 4 is an enlarged side view of the electrode-carrying basket and movable guide sheath shown in FIG. 1, with portions fragmented and in section, showing the electrode-carrying basket in a deployed condition;

FIG. 5 is a side view of two splines of the basket, when deployed, showing the arrangement of electrodes on the splines;

FIG. 6 is a section view taken generally along line 6—6 in FIG. 1, showing the interior of the catheter body for the mapping probe;

FIG. 7 is a plan view, with portions fragmented, of the introducer and outer guide sheath being introduced into the vein or artery access site in the process of forming the system shown in FIG. 1;

FIG. 8 is a plan view of the introducer, the outer guide sheath, and the steerable catheter being introduced into the access site in the process of forming the system shown in FIG. 1;

FIG. 9 is a plan view of the interior of the handle for the steerable catheter, partially broken away and in section, showing the mechanism for steering the distal tip of the catheter body;

FIG. 10 is a side view, with portions fragmented and in section, of advancing the steerable catheter body and outer guide sheath into the desired heart chamber;

FIG. 10A is a plan view of the interior of the hemostatic valve that systems embodying features of the invention use, showing the resilient slotted membrane present within the valve;

FIG. 11 is a side view, with portions fragmented and in section, of the guide sheath and the steerable catheter body advanced into the deployment position within the desired heart region;

FIG. 13 is a side view, with portions fragmented and in section, of the mapping probe being advanced through the hemostatic valve of the outer guide sheath, with the hemostat sheath fully forward to enclose the electrode-carrying basket;

FIG. 14 is a side view, with portions fragmented and in section, of the mapping probe after advancement through the hemostatic valve of the outer guide sheath, with the hemostat sheath pulled back to uncover the electrode-carrying basket;

FIG. 16 is an enlarged plan view of an alternative three dimensional structure, partially in section, that can be deployed using the system shown in FIG. 1, in use in association with a separate ablation probe;

FIG. 17 is an enlarged side section view of the structure shown in FIG. 16 in a collapsed condition before deployment;

FIG. 18 is an enlarged plan view of an alternative three dimensional structure that can be deployed using the system shown in FIG. 1, in use in association with a separate ablation probe;

FIG. 19 is an enlarged side section view of the structure shown in FIG. 18 in a collapsed condition before deployment;

FIG. 24 is a plan view, with portions fragmented and in section, of an integrated mapping and ablation system that embodies the features of the invention;

FIGS. 25 and 26 are enlarged side elevation views of the electrode-carrying basket of the mapping probe that the system shown in FIG. 24 uses, showing the range of movement of the steerable ablating element carried within the basket;

FIG. 27 is a diagrammatic view of the integrated mapping and ablation system shown in FIG. 24;

FIG. 28 is an end elevation view, taken generally along line 28—28 in FIG. 26, of the electrode-carrying basket of the mapping probe that the system shown in FIG. 24 uses, showing the range of movement of the steerable ablating element carried within the basket;

FIG. 29 is an enlarged side section view of the distal end of the electrode-carrying basket of the mapping probe that the system shown in FIG. 24 uses, showing the basket in a collapsed condition about the steerable ablating element before deployment;

FIG. 30 is an end section view of the collapsed basket, taken generally along line 30—30 in FIG. 29;

DESCRIPTION OF THE PREFERRED EMBODIMENTS

Figure 12:
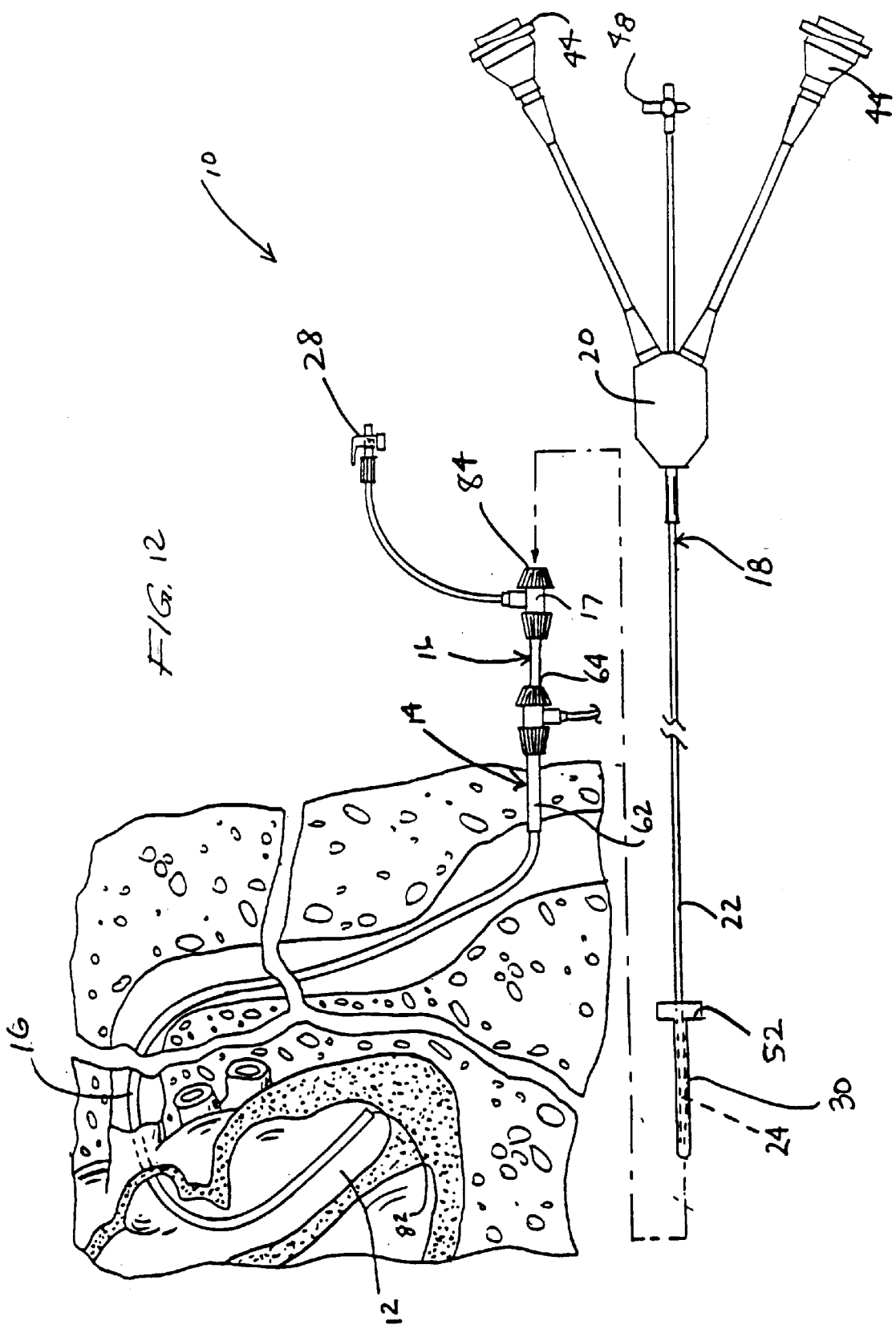
FIG. 12 is a side view, with portions fragmented and in section, of the mapping probe just before being introduced for advancement within the outer guide sheath, with the hemostat sheath fully forward to enclose the electrode-carrying basket.

FIG. 1 shows an endocardial mapping system 10 that embodies features of the invention, when deployed and ready for use within a selected region 12 inside the heart.

The Figures generally show the selected region 12 to be the left ventricle of the heart. However, it should be noted that the heart shown in the Figures is not anatomically accurate. The Figures show the heart in diagrammatic form to demonstrate the features of the invention.

When deployed, the system 10 includes an introducer 14, an outer guide sheath 16, and a mapping probe 18.

As FIG. 1 shows, the introducer 14 establishes access to a vein or artery. The outer guide sheath 16 enters the access through the introducer 14. The guide sheath 16 extends through the vein or artery to enter the selected heart chamber 12.

Together, the introducer 14 and the outer sheath 16 establish a passageway that guides the mapping probe 18 through the access vein or artery and into the selected heart chamber 12.

The mapping probe 18 has a handle 20 (which FIG. 12 shows in its entirety), an attached flexible catheter body 22, and a movable hemostat sheath 30 with associated carriage 52.

The distal end of the catheter body 22 carries a three dimensional structure 24. In FIG. 1, the structure 24 takes the form of a basket. FIGS. 16 and 18 show alternative structures, which will be described in greater detail later.

The three dimensional structure of the basket 24 includes an exterior surface 27 that encloses an open interior area 25. The basket 24 carries a three dimensional array of electrodes 26 on its exterior surface 27 (see FIG. 4 also).

As FIG. 1 shows, when deployed inside the heart chamber 12, the exterior surface 27 of the basket 24 holds the electrodes 26 against the endocardial surface.

When fully deployed, the outer guide sheath 16 holds the catheter body 22. The sheath 16 is made from an inert plastic material. In the preferred embodiment, the sheath 16 is made from a nylon composite material.

The sheath 16 has an inner diameter that is greater than the outer diameter of the catheter body 22. As a result, the sheath 16 can slide along the catheter body 22.

The proximal end of the sheath 16 includes a handle 17. The handle 17 helps the user slide the sheath 16 along the catheter body 22, as the arrows in FIGS. 1 and 2 depict. FIGS. 1 and 2 show the range of sheath movement.

As FIGS. 2 and 3 show, forward movement of the handle 17 (i.e., toward the introducer 14) advances the distal end of the slidable sheath 16 upon the basket 24, the slidable sheath 16 captures and collapses the basket 24 (as FIG. 3 also shows in greater detail). In this position, the distal end of the sheath 16 entirely encloses the basket 24.

As FIGS. 1 and 4 show, rearward movement of the handle 17 (i.e., away from the introducer 14) retracts the slidable sheath 16 away from the basket 24. This removes the compression force. The basket 24 opens to assume a prescribed three dimensional shape.

The basket electrodes 26 record the electrical potentials in myocardial tissue. Connectors 44 on the handle 20 (see FIGS. 12 and 13) attach to an external processor (not shown). The processor derives the activation times, the distribution, and the waveforms of the potentials recorded by the basket electrodes 26.

The basket 24 can be variously constructed. In the illustrated and preferred embodiment (best shown by FIG. 4), the basket 24 comprises a base member 32 and an end cap 34. Generally flexible splines 36 extend in a circumferentially spaced relationship between the base member 32 and the end cap 34.

In the illustrated embodiment, eight splines 36 form the basket 24. However, additional or fewer splines 36 could be used, depending upon application.

In this arrangement, the splines 36 are made of a resilient inert material, like Nitinol metal or silicone rubber. The splines 36 are connected between the base member 32 and the end cap 34 in a resilient, pretensed condition.

The resilient splines 36 bend and conform to the tissue surface they contact. As FIGS. 2 and 3 show, the splines 36 also collapse into a closed, compact bundle in response to an external compression force.

In the illustrated embodiment (as FIGS. 4 and 5 best show), each spline 36 carries eight electrodes 26. Of course, additional or fewer electrodes 26 can be used. Furthermore, one or more electrodes 26 can also be located on the end cap 34.

The electrodes 26 can be arranged in thirty-two bi-polar pairs, or as sixty-four uni-polar elements. In the preferred embodiment, the electrodes 26 are made of platinum or gold plated stainless steel.

A signal wire 38 made from a highly conductive metal, like copper, leads from each electrode 26. The signal wires 38 extend down the associated spline 36, by the base member 32, and into the catheter body 22. An inert plastic sheath 40 preferably covers each spline 36 to enclose the signal wires 38 (see FIGS. 4 and 5). In the preferred embodiment, the sheath 40 is made of polyurethane material.

The eight signal wires 38 for each spline 36 are twisted together to form a common bundle 42. As FIG. 6 shows, the eight common bundle 42 are, in turn, passed through the catheter body 22 of the mapping probe 18. The common bundles 42 extend within catheter body 22 and into the probe handle 20.

The sixty-four signal wires 38 are distributed within the probe handle 20 to one or more external connectors 44, as FIG. 12 shows. In the illustrated embodiment, each connector contains thirty-two pins to service thirty-two signal wires. The connectors 44 attach to the external processor.

As FIG. 6 shows, the catheter body 22 also includes an inner sleeve that forms a central lumen 46. The wire bundles 42 are oriented in an equally spaced array about this lumen 46. In the preferred embodiment, the sleeve of the central lumen 46 is made of a Teflon material.

The proximal end of the central lumen 46 is attached to a flushing port 48 that extends outside the handle 20, as FIG. 12 shows. The distal end of the central lumen 46 opens at the base member 32 of the basket 24. Anticoagulant or saline can be introduced through the flushing port 48 into the heart chamber 12 that the basket 24 occupies.

In the illustrated and preferred embodiment (as FIG. 5 best shows), a first region 54 on the proximal end of each spline 36 is free of electrodes 26. Likewise, a second region 56 on the distal end of each spline 36 is also free of electrodes 26. These two fore and aft regions 54 and 56 generally fail to make stable surface contact with the endocardial tissue. Therefore, electrodes 26 in these regions may not uniformly provide reliable signals.

The eight electrodes 26 on each spline 36 are arranged in 4 groups of equally spaced pairs in a third region 58 between the two end regions 54 and 56. The third region 58 uniformly makes stable surface contact with the endocardial tissue, creating reliable signals from the electrodes 26.

FIGS. 7 to 14 show the details of introducing the system 10 into the heart chamber 12.

The system 10 includes a steerable catheter 60 (see FIG. 8) to facilitate the introduction and positioning of the outer guide sheath 16.

The catheter 60 directs the introduction of the outer guide sheath 16, which is otherwise free of any onboard steering mechanism. The guide sheath 16, in turn, directs the introduction of the mapping probe 18, which is likewise free of any onboard steering mechanism.

Use of a separate catheter 60 for steering purposes results in a significant reduction in the overall size of the system components.

If the mapping probe 18 carried its own onboard steering mechanism, the catheter body 22 would have to be of sufficient size to accommodate it. Typically, this would require a catheter body 22 with a diameter of about 12–14 French (one French is 0.33 mm in diameter).

Furthermore, if carried onboard the mapping probe 18, the steering mechanism would also have to be of sufficient strength to deflect the entire structure of the basket 24 when in a collapsed condition.

According to this aspect of the invention, use of a separate, dedicated steerable catheter 60 permits the introduction of the entire system 10 through the access vessel and into the heart chamber using an outer guide sheath of about only 10 French. The catheter body 22 of the mapping probe 18 can also be significantly smaller, being on the order of 6 to 8 French. In addition, a smaller steering mechanism can also be used, because only the outer sheath 16 needs to be steered.

As FIG. 7 shows, the introducer 14 has a skin-piercing cannula 62. The physician uses the cannula 62 to establish percutaneous access into the selected vein or artery (which is typically the femoral vein or artery). The other end of the introducer 14 includes a conventional hemostatic valve 64.

The valve 64 includes a resilient slotted membrane 65 (as FIG. 10A shows). The slotted membrane 65 blocks the outflow of blood and other fluids from the access. The slot in the membrane 65 yields to permit the introduction of the outer guide sheath 16 through it. The resilient membrane 65 conforms about the outer surface of the sheath 16, thereby maintaining a fluid tight seal.

The introducer 14 also includes a flushing port 66 for introducing anticoagulant or other fluid at the access site.

As FIG. 8 shows, the steerable catheter 60 includes a catheter body 68 having a steerable tip 70 at its distal end. A handle 72 is attached to the proximal end of the catheter body 68. The handle 12 encloses a steering mechanism 74 for the distal tip 70.

The steering mechanism 74 can vary. In the illustrated embodiment (see FIG. 9), the steering mechanism is the one shown in Copending U.S. application Ser. No. 07/789,260, which is incorporated by reference.

As FIG. 9 shows, the steering mechanism 74 of this construction includes a rotating cam wheel 76 within the handle 72. An external steering lever 78 rotates the cam wheel. The cam wheel 76 holds the proximal ends of right and left steering wires 80.

The steering wires 80 extend along the associated left and right side surfaces of the cam wheel 76 and through the catheter body 68. The steering wires 80 connect to the left and right sides of a resilient bendable wire or spring (not shown) that deflects the steerable distal tip 70 of the catheter body 68.

As FIG. 8 shows, forward movement of the steering lever 80 bends the distal tip 70 down. Rearward movement of the steering lever 80 rearward bends the distal tip 70 up. By rotating the handle 70, thereby rotating the distal tip 70, and thereafter manipulating the steering lever 80 as required, it is possible to maneuver the distal tip 70 virtually in any direction.

In an alternative arrangement (shown in phantom line view A in FIG. 8), the steerable distal tip 70 can also be bent out of a normal coaxial relationship with the catheter body 68 using custom shaped wire stiffeners 71. The stiffeners 71 create a pre-formed, complex curve configuration. The complex curvature simplifies access to difficult-to-reach locations within the heart, such as the aortic approach through the left ventricle to the left atrium.

FIGS. 10 and 11 show the details of using the steerable catheter 60 to guide the outer sheath 16 into position.

The outer guide sheath 16 includes an interior bore 82 that receives the steerable catheter body 68 of the catheter 60. The physician can slide the outer guide sheath 16 along the steerable body 68 of the catheter 60.

The handle 17 of the outer sheath 16 includes a conventional hemostatic valve 84. The valve 84, like the valve 64, includes a resilient slotted membrane 65 (as FIG. 10A shows) that blocks the outflow of blood and other fluids. Like the valve 64, the slotted membrane 65 yields to permit the introduction of the body 22 of the mapping probe 18 through it. At the same time, the membrane 65 conforms about the outer surface of the body 22 to maintain a fluid tight seal.

Together, the valves 64 and 84 provide an effective hemostatic system that allows a procedure to be performed in a clean and relatively bloodless manner.

In use, the steerable catheter body 68 enters the bore 82 of the guide sheath 16 through the valve 84, as FIG. 10 shows. The handle 17 of the outer sheath 16 also preferably includes a flushing port 28 for the introduction of an anticoagulant or saline into the interior bore 82.

As FIG. 10 also shows, the physician advances the catheter body 68 and the outer guide sheath 16 together through the access vein or artery. The physician retains the sheath handle 17 near the catheter handle 72 to keep the catheter tip 70 outside the distal end of the outer sheath 16. In this way, the physician can operate the steering lever 78 to remotely point and steer the distal end 70 of the catheter body 68 while jointly advancing the catheter body 68 and guide sheath 16 through the access vein or artery.

The physician can observe the progress of the catheter body 68 using fluoroscopic or ultrasound imaging, or the like. The outer sheath 16 can include an radio-opaque compound, such a barium, for this purpose. Alternatively, a radio-opaque marker can be placed at the distal end of the outer sheath 16.

This allows the physician to maneuver the catheter body 68 through the vein or artery into the selected interior heart chamber 12, as FIG. 10 shows.

As FIG. 11 shows, when the physician locates the distal end 70 of the catheter body 68 in the desired endocardial chamber 12, he/she slides the outer sheath handle 17 forward along the catheter body 68, away from the handle 72 and toward the introducer 14. The catheter body 68 directs the guide sheath 16 fully into the heart chamber 12, coextensive with the distal tip 70.

Holding the handle 17 of the outer sheath 16, the physician withdraws the steerable catheter body 68 from the outer guide sheath 16.

The system 10 is now deployed in the condition generally shown in FIG. 12. As FIG. 12 shows, the guide sheath bore 82 establishes a passageway that leads directly from the introducer 14 into the selected heart chamber 12. The mapping probe 18 follows this passageway for deployment inside the chamber 12.

As FIG. 12 shows, before introducing the mapping probe 18, the physician advances the hemostat sheath 30, by pushing on the carriage 52. The sheath 30 captures and collapses the basket 24.

As FIG. 13 shows, the physician introduces the hemostat sheath 30, with enclosed basket 24, through the hemostatic valve 84 of the outer sheath handle 17. The hemostat sheath 30 protects the basket electrodes 26 from damage during insertion through the valve 84.

As FIG. 14 shows, when the catheter body 22 is advanced approximately three inches into the guide sheath 16, the physician pulls back on the sheath carriage 52 to withdraw the hemostat sheath 30 from the valve 84. The hemostat valve 84 seals about the catheter body 22. The guide sheath 16 now itself encloses the collapsed basket 24.

As FIG. 2 shows, the outer sheath 16 directs the basket 24 of mapping probe 18 to the desired location inside the heart chamber 12. As FIG. 1 shows, the physician then moves the handle 17 rearward. The distal end of the sheath 16 slides back to deploy the basket 24 for use.

Once deployed, the physician can again collapse the basket 24 (by pushing forward on the handle 17), as FIG. 2 shows. The physician can then rotate the sheath 16 and probe 18 to change the angular orientation of the basket electrodes 26 inside the chamber 12, without contacting and perhaps damaging endocardial tissue. The physician can then redeploy the basket 24 in its new orientation by pulling back on the handle 17, as FIG. 1 shows.

The physician analyses the signals received from the basket electrodes 26 to locate likely efficacious sites for ablation.

The physician can now takes steps to ablate the myocardial tissue areas located by the basket electrodes 26. The physician can accomplish this result by using an electrode to thermally destroy myocardial tissue, either by heating or cooling the tissue. Alternatively, the physician can inject a chemical substance that destroys myocardial tissue. The physician can use other means for destroying myocardial tissue as well.

The illustrated and preferred embodiment accomplishes ablation by using an endocardial electrode to emit energy that heats myocardial tissue to thermally destroy it. The energy is transmitted between the endocardial electrode and an exterior indifferent electrode on the patient.

The type of ablating energy can vary. It can, for example, be radio frequency energy or microwave energy. The ablating energy heats and thermally destroys the tissue to form a lesion, thereby restoring normal heart rhythm.

Ablating energy can be conveyed to one or more electrodes 26 carried by the basket 24. In this way, one or more of the sensing electrodes 26 on the basket 24 can also be used for tissue ablation.

Figure 15:
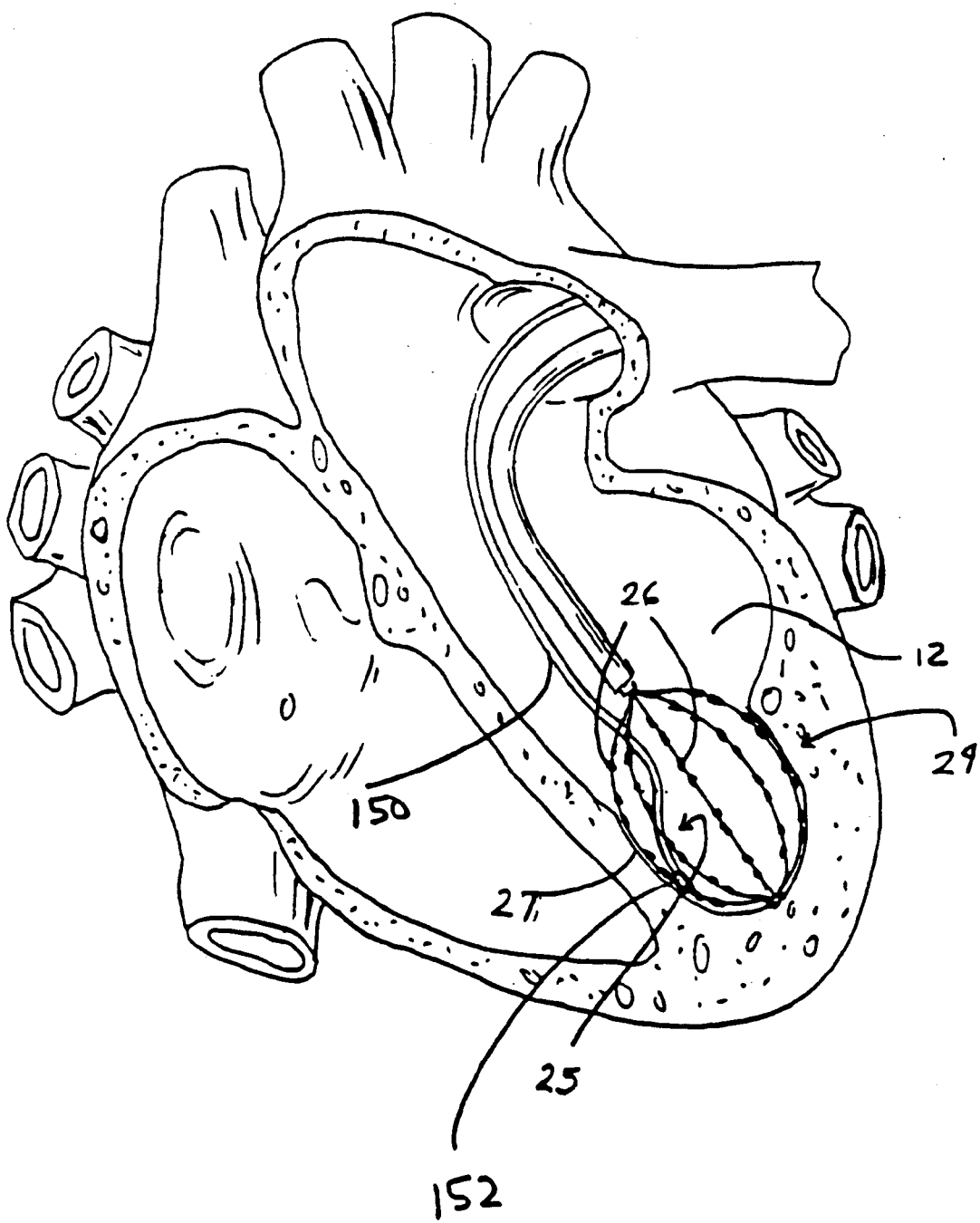
FIG. 15 is an enlarged view, with portions in section, of the electrode-carrying basket deployed inside the heart chamber in use in association with a separate ablation probe.

As FIG. 15 shows, an external steerable ablating probe 150 can be used in association with the basket 24. The physician steers the probe 150 under fluoroscopic control to maneuver the ablating element 152 into the basket 24. Once inside the basket 24, the physician steers the ablating element 152 into contact with the tissue region identified by the basket electrodes 26 as the likely efficacious site for ablation. The physician then conveys ablating energy to the element 152.

In this arrangement, the basket 24 serves, not only to identify the likely ablation sites, but also to stabilize the external ablating probe 150 within a confined region within the heart chamber 12.

FIGS. 16 and 17 show an alternative configuration for a three dimensional structure 154 that the mapping probe 18 can carry.

In this embodiment, the structure 154 comprises a single length of inert wire material, such a Nitinol metal wire, preformed into a helical array. While the particular shape of the helical array can vary, in the illustrated embodiment, the array has a larger diameter in its midsection than on its proximal and distal ends.

As FIG. 16 shows, the structure 154 can be used to stabilize the external steerable ablation probe 150 in the same fashion as the basket 24 shown in FIG. 15 does.

The structure 154 can also carry electrodes 156, like the basket 24, for mapping and/or ablating purposes.

As FIG. 17 shows, the structure 154 can be collapsed in response to an external compression force. The distal end of the slidable guide sheath 16 provides this compression force to retract and deploy the structure 154 inside the selected heart chamber, just like the basket structure 24.

FIGS. 18 and 19 show yet another alternative configuration for a three dimensional structure 158 that can be carried by the mapping probe 18. In this embodiment, the structure 158 comprises two independent loops 160 and 162 of inert wire material, such a Nitinol metal wire.

The loop 160 nests within the loop 162. The distal ends of the nested loops 160 and 162 are not joined. Instead, the nested loops 160 and 162 are free to flex and bend independently of each other.

In the illustrated configuration, the loops 160 and 162 form right angles to each other. Of course, other angular relationships can be used. Additional independent loops can also be included to form the structure 158.

As FIG. 18 shows, the loop structure 158 can be used to stabilize the external steerable probe 150 in the same fashion as the structures 24 and 154 shown in FIGS. 15 and 16 do.

One or more of the loops 160 and 162 can also carry electrodes 164 for mapping and/or ablating purposes.

As the previous structures 24 and 154, the structure 158 can be collapsed in response to an external compression force, as FIG. 19 shows. The distal end of the slidable guide sheath 16 provides this compression force to retract and deploy the structure 158 inside the selected heart chamber 12.

Figure 20:
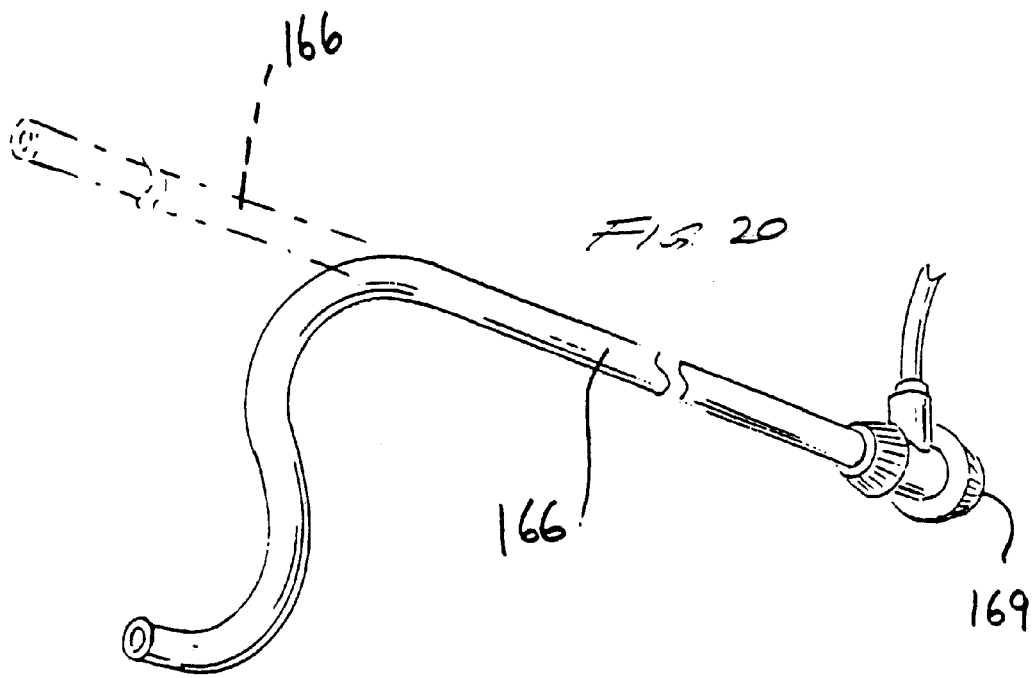
FIG. 20 is a perspective view, partially fragmented, of an alternative embodiment of an outer guide sheath having a preformed complex curvature.
Figure 21:
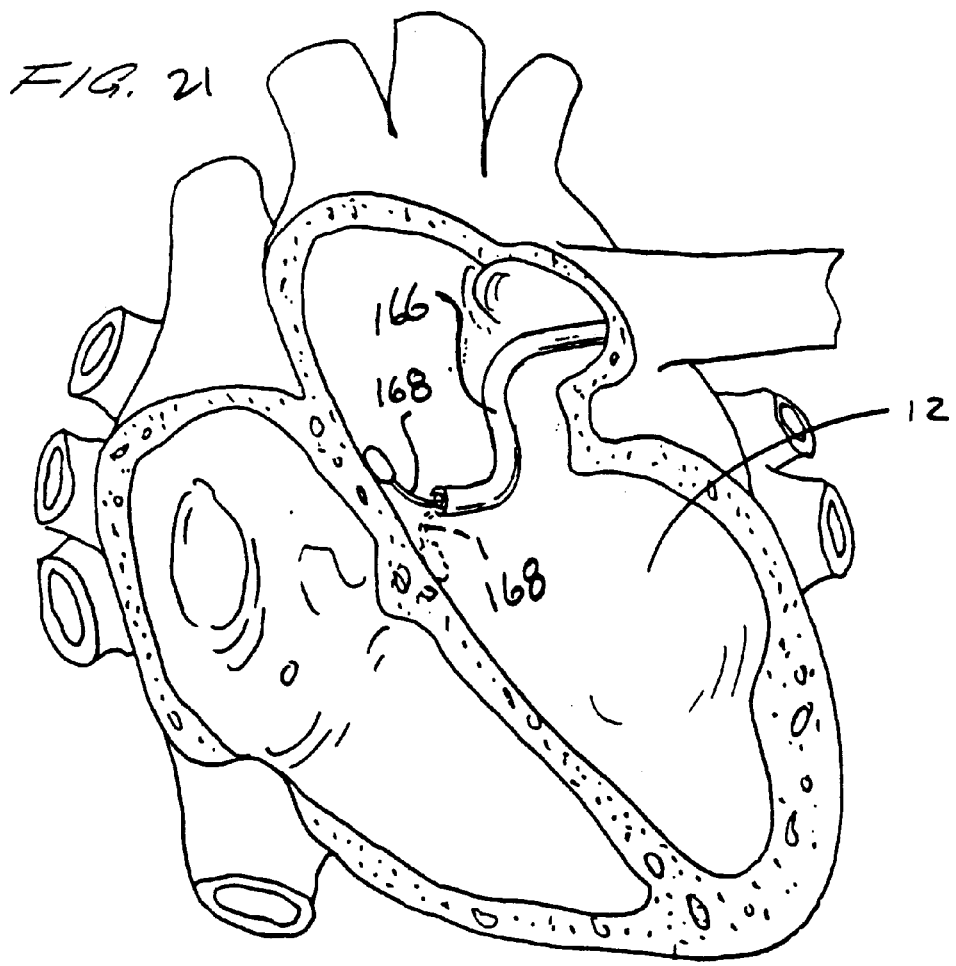
FIG. 21 is an enlarged plan view, partially in section, of the guide sheath shown in FIG. 20 deployed inside the heart chamber and in use in association with a separate steerable ablation probe.

FIGS. 20 and 21 show an alternative embodiment of a guide sheath 166 that can be used in association with the introducer 14 to locate a steerable ablation probe 168 inside the selected heart chamber 12.

Unlike the guide sheath 22, the guide sheath 166 is preformed with a memory that assumes a prescribed complex curvature in the absence of an external stretching or compressing force.

FIG. 20 shows in phantom lines the guide sheath 166 in a stretched or compressed condition, as it would be when being advanced along the steerable catheter body 68 through the access vein or artery.

Upon entering the less constricted space of the heart chamber 12, as FIG. 21 shows, the sheath 166 assumes its complex curved condition. The complex curve is selected to simplify access to difficult-to-reach locations within the heart, such as through the inferior vena cava into the right ventricle, as FIG. 21 shows.

Like the sheath 16, the sheath 166 preferably includes a conventional hemostatic valve 169 on its proximal end. As previously described, the hemostatic valve 169 includes a resilient slotted membrane to block the outflow of fluids, while allowing passage of a catheter body.

FIG. 21 shows the sheath 166 in use in association with a steerable ablating probe 168, which enters the sheath 166 through the hemostatic valve 169. The sheath 166, like the sheath 16, guides the probe 168 through the access vein or artery into the heart chamber 12.

The complex curvature of the sheath 166 more precisely orients the steerable ablation probe 168 with respect to the intended ablation site than the sheath 16. As FIG. 21 shows, the complex curvature points the distal end of the sheath 166 in a general orientation toward the intended ablation site. This allows the physician to finally orient the ablating element 170 with the intended site using fine steering adjustments under fluoroscopic control.

The embodiment shown in FIGS. 20 and 21 uses the preformed sheath 166 to provide relatively coarse steering guidance for the ablation probe 168 into the heart chamber 12. The sheath 166 simplifies the task of final alignment and positioning of the ablating element with respect to the precise ablation region, which the physician can accomplish using a few, relatively fine remote steering adjustments.

Figure 22:
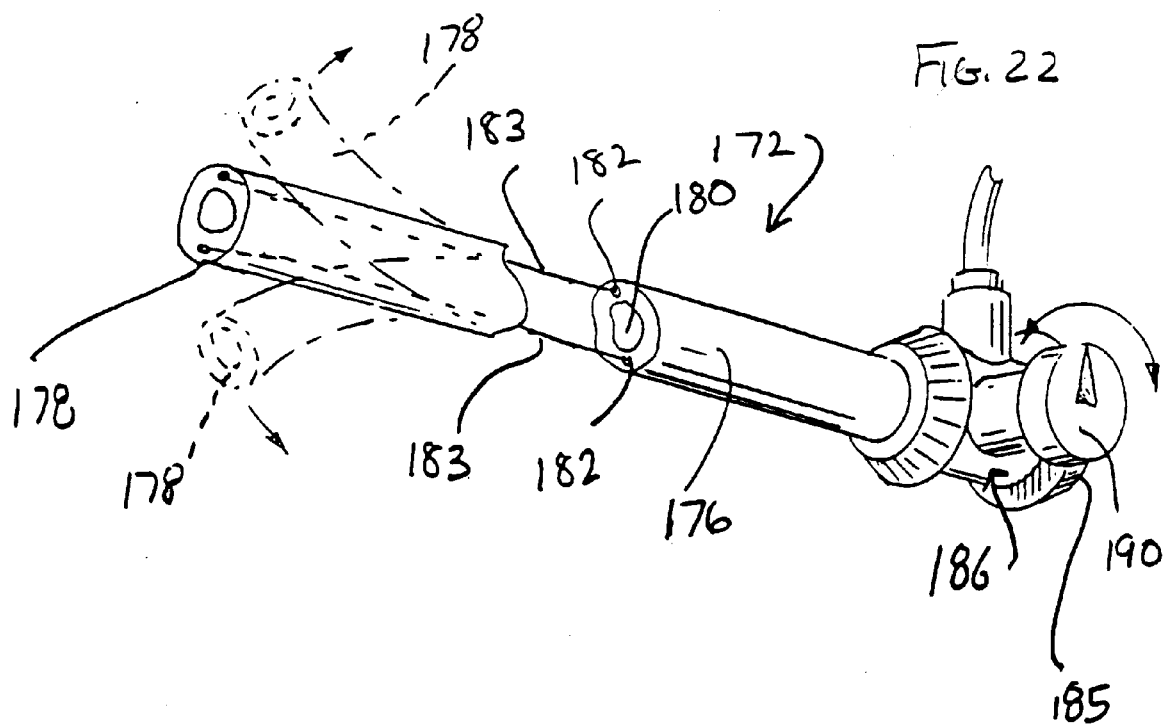
FIG. 22 is a perspective view, partially fragmented, of an alternative embodiment of an outer guide sheath having a steerable distal tip.
Figure 23:
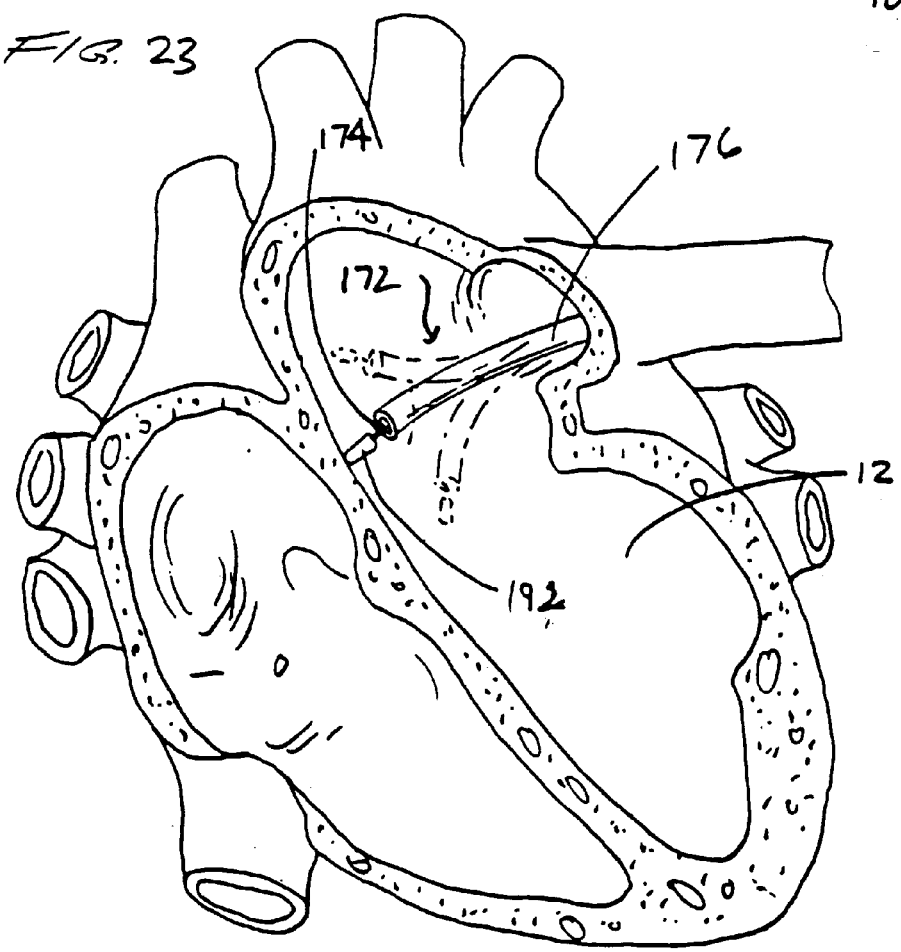
FIG. 23 is an enlarged plan view, partially in section, of the guide sheath shown in FIG. 22 deployed inside the heart chamber and in use in association with a separate ablation probe.

FIGS. 22 and 23 show yet another alternative embodiment of a guide sheath 172 that can be used in association with the introducer 14 to locate an ablation probe 174 inside the selected heart chamber 12.

In FIGS. 22 and 23, the guide sheath 172 includes a sheath body 176 with a steerable distal tip 178. As FIG. 22 shows, the sheath body 176 is extruded to include a center guide lumen 180 and two side lumens 182. Steering wires 183 extend through the side lumens 182, which are located near the exterior surface of the body 176.

The distal ends of the steering wires 183 are attached to the side lumens 182 at the distal tip 178 of the sheath body 176. The proximal ends of the steering wires 183 are attached to a steering mechanism 186 within a handle 188 attached at the proximal end of the sheath body 176.

The steering mechanism 186 can vary. In the illustrated embodiment, the mechanism 186 is the rotating cam arrangement shown in FIG. 9. In this arrangement, the steering mechanism 186 includes an exterior steering lever 190. Fore and aft movement of the steering lever 190 deflects the distal tip 178 of the guide sheath 176, as FIG. 22 shows.

Like the sheath 16, the sheath 172 preferably includes a conventional hemostatic valve 185 on its proximal end to block the outflow of fluids while allowing the passage of a catheter body.

The steerable guide sheath 172 is used in association with the introducer 14. The physician steers the guide sheath 172 through the access vein or artery and into the selected heart chamber 12 under fluoroscopic control, as FIG. 23 shows. The physician then introduces the probe 174 through the center guide lumen 180.

In this arrangement, the probe 174 can carry a mapping structure, like those shown in FIGS. 1; 16; and 18. Alternatively (as FIG. 23 shows), the probe 174 carries an ablating element 192.

Because the guide sheath 174 is itself the catheter body 194 of the probe 174 need not include a steering mechanism. The catheter body 194 need only carry the electrical conduction wires its function requires. The catheter body 194 can therefore be downsized. Alternatively, the absence of a steering mechanism frees space within the catheter body 194 for additional or larger electrical conduction wires, as ablating elements using coaxial cable or temperature sensing elements may require.

FIG. 24 shows an integrated system 86 for performing endocardial mapping and ablation.

Like the first described system 10, the integrated system 86 includes a mapping probe 18 with sensing electrodes 26 carried by a three dimensional basket 24. In addition, the integrated system 86 includes, as an integral part, a steerable ablating element 88 that is carried within the open interior area 25 of the basket 24.

The ablating element 88 can be moved relative to the sensing electrodes 26 in three principal directions. First, the ablating element 88 moves along the axis of the mapping probe body 96. Second, the ablating element 88 moves rotationally about the axis of the mapping probe body 96. Third, the ablating element 88 moves in a direction normal to the axis of the mapping probe body 96. FIGS. 25 to 28 show the range of movement the preferred embodiment provides.

Movement of the ablating element 88 does not effect the contact between the sensing electrodes 26 and the endocardial tissue. In other words, the electrodes 26 and the ablating element 88 are capable of making contact with endocardial tissue independent of each other.

More specifically, the system 86 includes a steerable ablation catheter 90 that is an integral part of the mapping probe 18. The ablation catheter 90 includes a steering assembly 92 with a steerable distal tip 84. The steerable distal tip 84 carries the ablating element 88.

As FIG. 27 shows diagrammatically, the mapping probe 18 includes a catheter body 96 through which the steering assembly 92 of the ablation catheter 90 passes during use. The proximal end of the catheter body 96 communicates with an opening at the rear of the handle 20. The distal end of the catheter body 96 opens into the interior area 25 of the basket 24. A conventional hemostatic valve 95 is located at this junction. As previously described, the valve 95 includes a resilient slotted membrane that blocks the outflow of fluid while allowing the passage of the steering assembly 92.

The proximal end of the steering assembly 92 of the ablation catheter 90 is attached to a handle 98 (as FIG. 24 best shows). By pulling and pushing the handle 98, the physician moves the ablating element 88 along the axis of the mapping probe body 96. By rotating the handle 98, the physician rotates the ablating element 88 about the axis of the mapping probe body 96.

The handle 98 further encloses a steering mechanism 74 for the tip 84. The steering mechanism 74 for the ablating catheter 90 is the same as the steering mechanism 74 for the catheter 60 used in the first described system 10, and thereby shares the same reference number.

As FIG. 27 generally shows, movement of the steering lever 78 forward bends the distal tip 84, and with it, the ablating element 88, down. Movement of the steering lever 78 rearward bends the distal tip 84, and with it, the ablating element 88, up.

FIGS. 25 and 26 also show the movement of the distal tip 84 and element 88 through the basket 24 between a generally straight configuration (FIG. 25) and a deflected position, placing the ablating element 88 in contact with endocardial tissue (FIG. 26).

By coordinating lateral (i.e., pushing and pulling) movement of the handle 98 with handle rotation and tip deflection, it is possible to move the ablating element 88 in virtually any direction normal to the axis of the catheter body 96, as FIG. 28 shows.

By rotating and moving the handle 98 in these ways, it is possible to maneuver the ablating element 88 under fluoroscopic control through the basket 24 into contact with any point of the endocardial surface of the chamber 12. The ablating 88 can be moved through the basket 24 to tissue locations either in contact with the exterior surface of the basket 24 or laying outside the reach of the basket 24 itself.

A cable 100 with an outer insulating sheath is attached to the ablating element 88 (see FIGS. 27 and 29). The electrically insulated cable 100 extends down the length of the steering assembly 92. The cable 100 conveys ablating energy to the element 88.

A plug 102 attached to the proximal end of the cable 100 (see FIGS. 24 and 27) extends outside the handle 98 for connection to a source of ablating energy (not shown).

The integrated mapping and ablation system 86 shown in FIG. 24 shares various other components and methodologies with the first described system 10. Elements shared by the two embodiments are given common reference numbers.

The integrated system 86 uses the same introducer 14 to establish an access. It also uses the same outer guide sheath 16 and the same steerable catheter 60 (with steerable catheter body 68) to position the outer guide sheath 16. The outer sheath 16 is inserted through the introducer 14 and positioned inside the heart by the steerable catheter body 68 in the same fashion as earlier described (and as shown in FIGS. 10 and 11).

As also earlier described (and as FIG. 2 shows), the mapping probe 18 is guided by the outer sheath 16 into position. The mapping probe 18 in the integrated system 86 also includes the slidable sheath 16 to enclose and deploy the basket 24, in the same manner as earlier described. When enclosed by the sheath 16, the basket 24 collapses about the distal tip 94 and ablating element 88 (as FIGS. 29 and 30 show).

In use, the physician guides the mapping probe 18 with integral ablating catheter 90 into position through the outer sheath 16. The physician then deploys the basket 24, freeing the ablating element 88 for use, as FIG. 24 shows.

As FIG. 24 shows, the basket structure contacts the surrounding endocardial tissue to hold and stabilize the ablating element 88 in a desired confined region within the heart while the basket electrodes 26 provide mapping signals. The ablating element 88 can be remotely steered to sites identified by the basket electrodes 26 (as FIG. 26 shows). Ablating energy can then be applied to thermally destroy the tissue.

As in the first described embodiment, the basket electrodes 26 can be used for ablation purposes, too.

Figure 31:
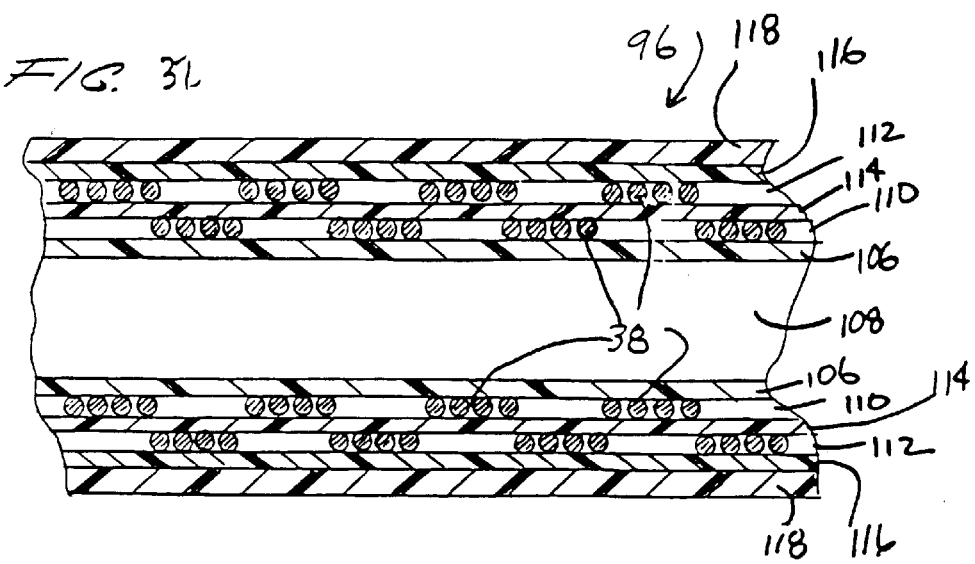
FIG. 31 is a side section view of the multiple layer catheter body of the mapping probe used in the system shown in FIG. 24.
Figure 32:
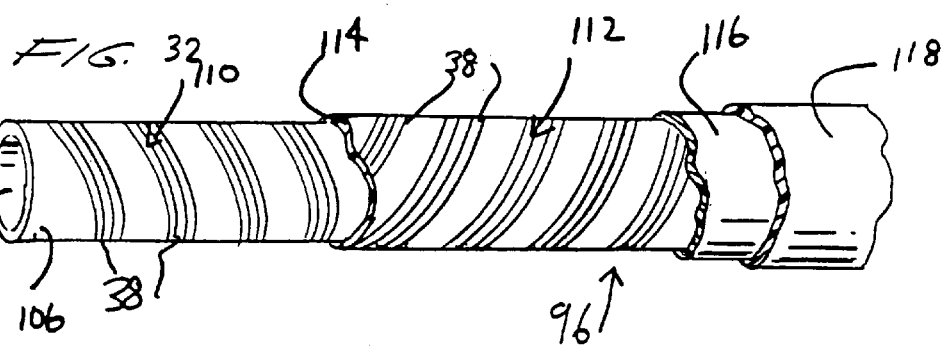
FIG. 32 is a perspective view of the multiple layers of the catheter body shown in section in FIG. 31.

As FIGS. 31 and 32 show, the catheter body 96 of the mapping probe 18 comprises an integral multiple layer structure. In this structure, the signal wires 38 for the sensing electrodes 26 on the basket 24 are imbedded within the walls of the catheter body 96. This structure frees space at the interior of catheter body 96 to accommodate passage of the steering assembly 92.

As FIGS. 31 and 32 show, the catheter body 96 includes a center tube 106 made from a plastic material, such as Pebax tubing. The center tube 106 has an interior bore 108 of a size that accommodates the steering assembly 92 of the ablating catheter 90.

The catheter body 96 includes two layers 110 and 112 of copper signal wire 38 (42 gauge) wrapped about the center tube 106. Each copper signal wire 38 carries an outer insulating sheath. In addition, the two layers 110 and 112 are separated from each other by an insulation layer 114 of Teflon plastic or the like. The layer 114 provides an added measure of insulation between the wires 38, particularly in regions where point contact between the overlapping wire layers 110 and 112 could occur.

In the illustrated embodiment, where the basket 24 has sixty-four electrodes, each layer 110 and 112 carries eight groups of four signal wires 38. The signal wires 38 are preferably wound helically along the length of the catheter body 96.

The catheter body 96 further includes a metalized plastic layer 116 (such as metalized polyamide) that surrounds the second layer 112 of signal wires 38. The layer 116 protection against electromagnetic interference (EMI). The layer 116 is, in turn, enclosed within an outer plastic tube 118 of a material such as Pebax.

FIGS. 33 to 38 show a process for making the multiple layer catheter body 96.

Figure 33:
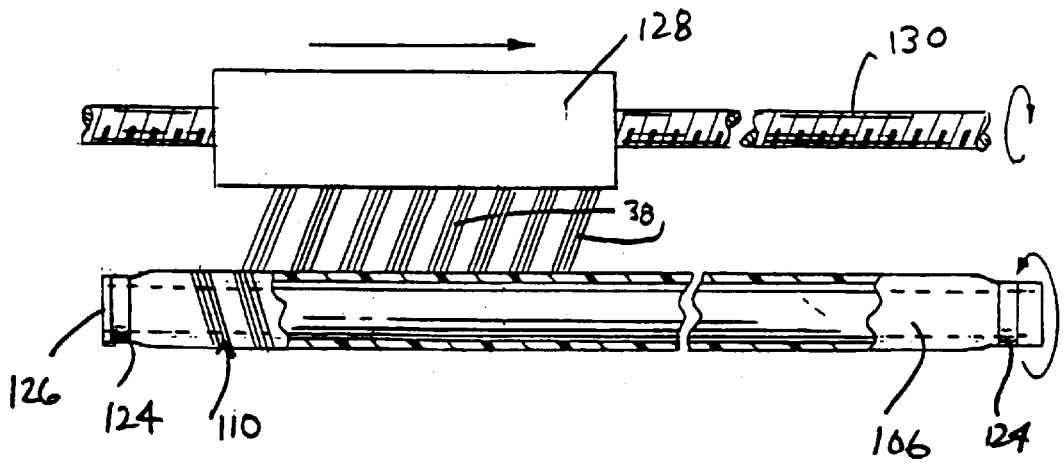
FIG. 33 is a view, partially in section, showing the formation of the first layer of the multiple layer catheter body shown in FIGS. 31 and 32.

As FIG. 33 shows, the center tube 106 is fastened by clamps 124 to a mandrel 126. The mandrel 126 is rotated during the assembly process. In the illustrated embodiment, the mandrel 126 rotates in a clockwise direction.

A wire holder 128 dispenses thirty-two shielded signal wires 38 in eight groups of four each. During the assembly process, the holder 128 advances along the axis of the mandrel 126 upon a rotating lead screw 130. In the illustrated embodiment, the lead screw 130 is rotated clockwise to advance the holder 128 from left to right along the axis of the rotating mandrel 126.

By synchronizing the rotation of the mandrel 126 with the translation of the holder 128, the wire groups dispensed by the holder 128 are helically wrapped about the center tube 106. This forms the first layer 110 of signal wires 38 about the center tube 106.

Figure 34:
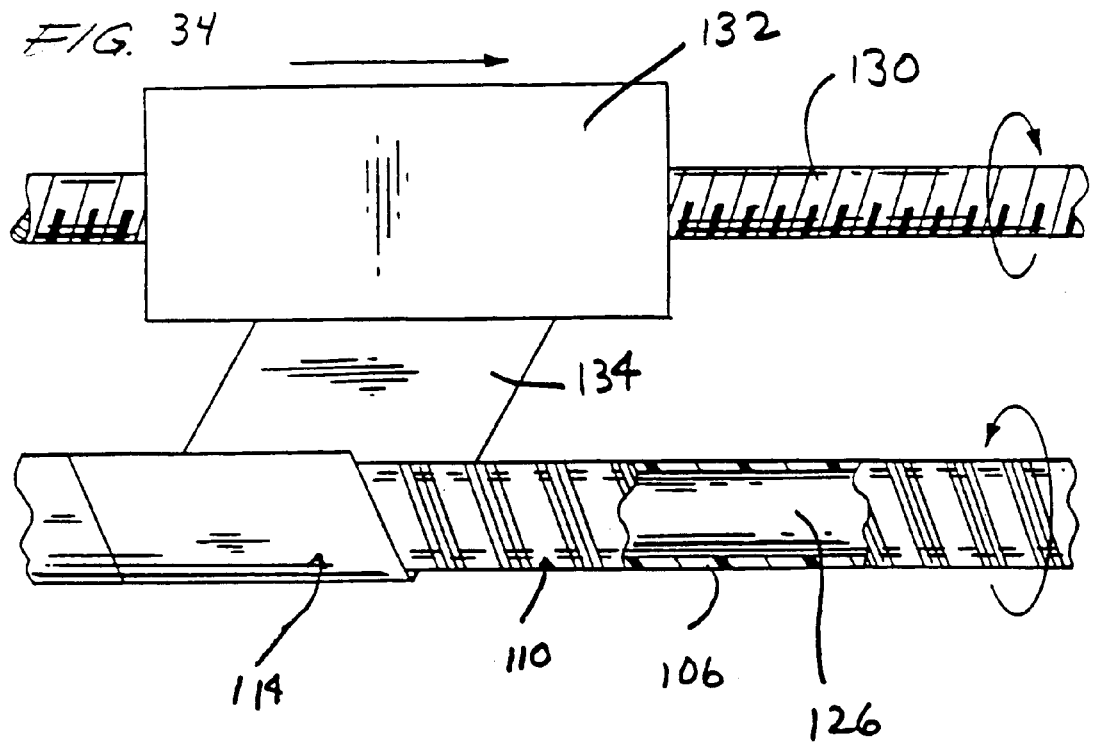
FIG. 34 is a view, partially in section, showing the formation of the second layer of the multiple layer catheter body shown in FIGS. 31 and 32.

As FIG. 34 shows, another holder 132 is advanced by the lead screw 130 along the axis of the rotating mandrel 126. The holder 132 helically wraps insulating Teflon plastic tape 134 about the first layer 110 of signal wires 38. This forms the added insulating layer 114 of the catheter body 96.

Figure 35:
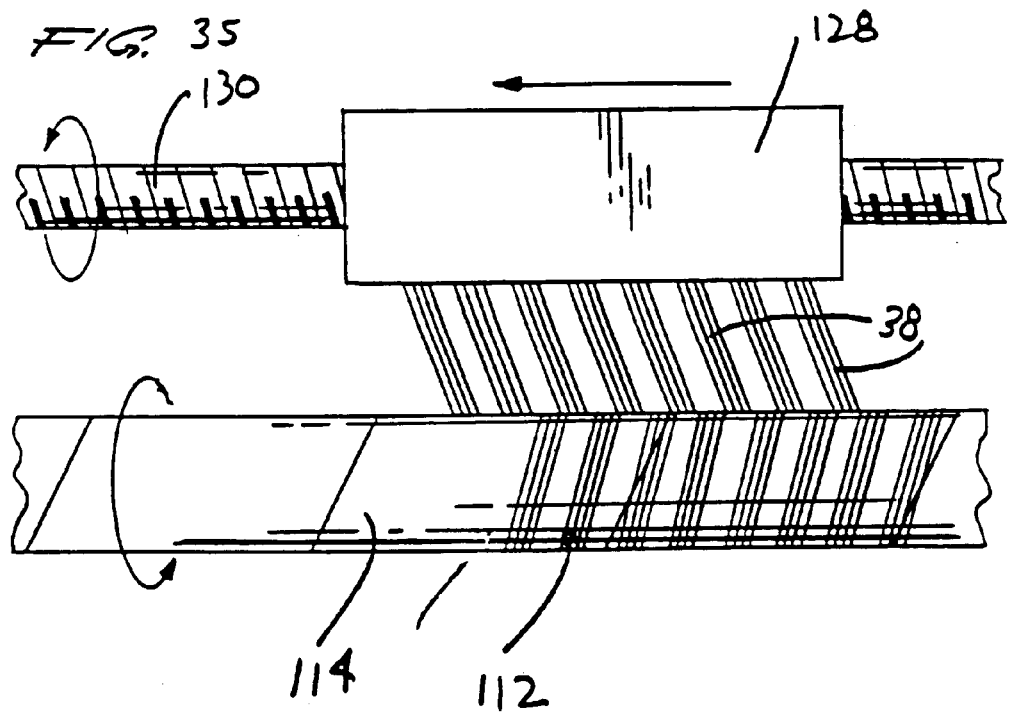
FIG. 35 is a view showing the formation of the third layer of the multiple layer catheter body shown in FIGS. 31 and 32.

As FIG. 35 shows, the wire holder 128 is again advanced by the lead screw 130 along the axis of the rotating mandrel 126, which during this step is rotated counterclockwise. The holder 128 dispenses thirty-two additional signal wires 38 in eight groups of four each about the insulating layer 114. The rotating lead screw 130 advances the holder 128 from right to left while the mandrel 126 rotates counterclockwise to helically wrap the second layer 112 of signal wires 38 about the insulating layer 114, counterwound to the first layer 110.

The counterwinding of the signal wire layers 110 and 112 provides greater torque transmission for rotating the basket 24 in response to rotating the handle 20. While counterwinding is preferred for this reason, the signal wire layers 110 and 112 can be wrapped in the same direction.

Figure 36:
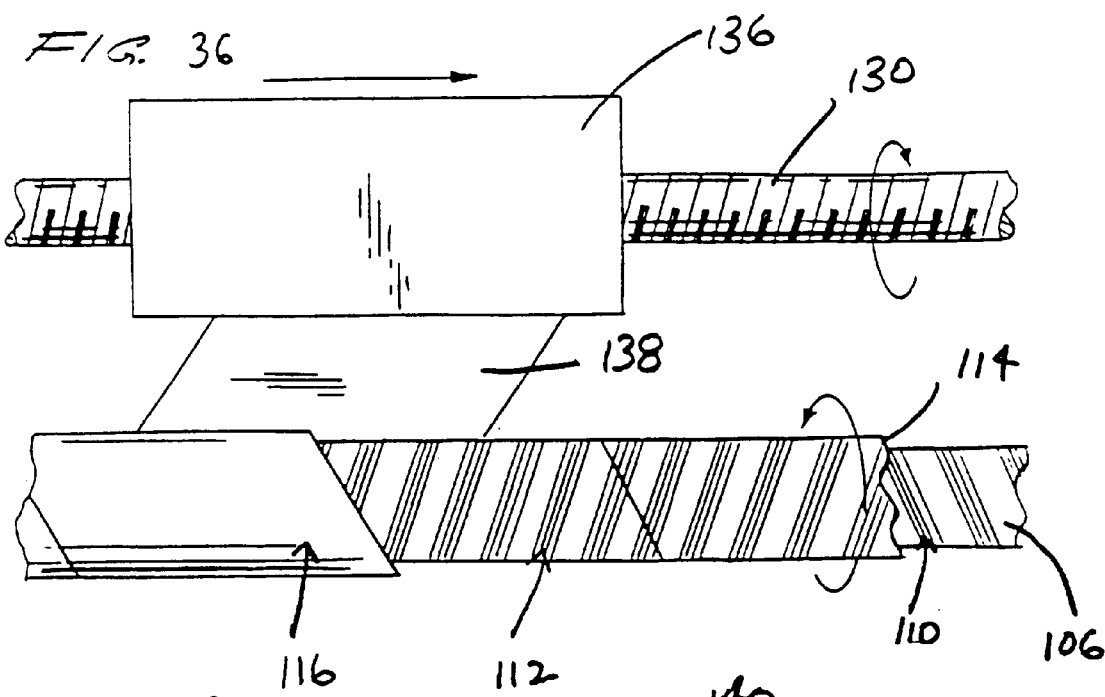
FIG. 36 is a view showing the formation of the fourth layer of the multiple layer catheter body shown in FIGS. 31 and 32.

As FIG. 36 shows, another holder 136 is advanced by the lead screw 130 along the axis of the rotating mandrel 126. The holder 136 helically wraps metalized plastic material 138 about the second wire layer 112, creating the EMI shield layer 116.

Figure 37:
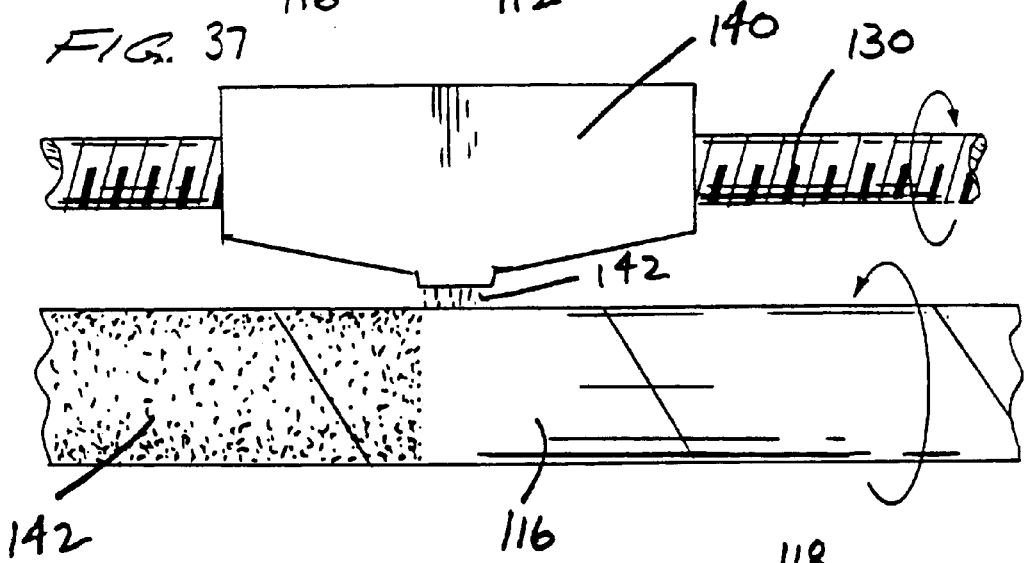
FIGS. 37 and 38 are views showing the formation of the fifth and final layer of the multiple layer catheter body shown in FIGS. 31 and 32.

As FIG. 37 shows, another holder 140 advanced by the lead screw 130 dispenses adhesive 142 upon the metalized layer 116.

Figure 38:
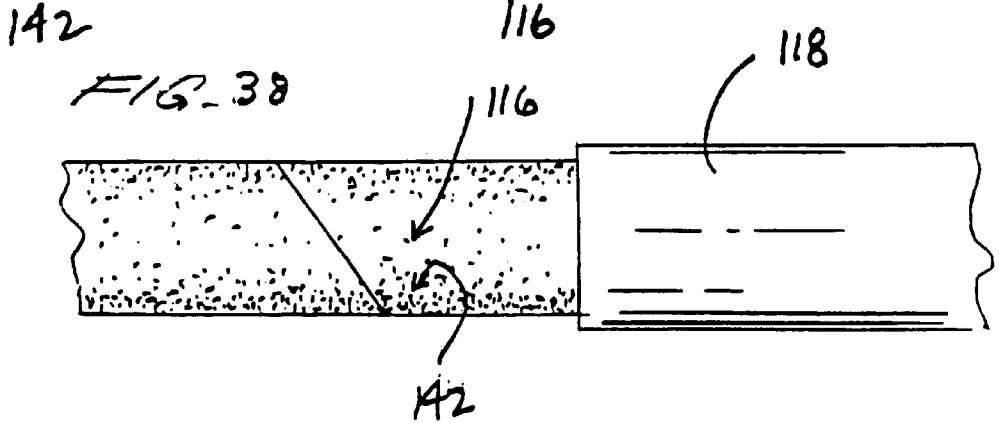

As FIG. 38 shows, the outer sleeve 118 is pulled over the adhesive 142 to complete the structure of the multiple layer catheter body 96.

Various features of the invention are set forth in the following claims.

What is claimed is:

1. A method of using a probe assembly within a heart, the comprising the steps of:

providing a probe assembly having a catheter body with a distal end, an ablating element integrally attached to the catheter body and extending distally beyond the distal end of the catheter body, a support structure integrally attached to the catheter body and extending distally beyond the distal end about an axis for contacting surrounding tissue in the heart, and a steering element integrally carried by the catheter body and connected to the ablating element for moving the ablating element with respect to the support structure, introducing the catheter body, ablating element and support structure together as an integrated assembly into and advancing it through a patient's vasculature with the support element collapsed about the ablating element, bringing the support structure into contact with heart tissue by expanding the support structure about the ablating element, bringing the ablating element into contact with heart tissue while maintaining contact between the support structure and heart tissue by operating the steering element to move the ablating element into contact with heart tissue, transmitting ablation energy to the ablating element while contacting heart tissue, completely collapsing the support structure about the ablating element, and withdrawing the integrated probe assembly from the patient vasculature while the support structure is completely collapsed about the ablating element.

2. The method of claim 1, wherein the ablating element is adapted to move in a first direction along the axis of the support structure, in a second direction rotating about the axis of the support structure, and in a third direction normal to the axis of the support structure, and the method further includes the step of moving the ablating element in at least the three directions.

3. The method of claim 1, further including at least one electrode element carried by the support structure operative for sensing electrical activity in the tissue, and the method further includes the step of sensing electrical activity in the tissue with said at least one electrode element carried by the support structure.

4. The method of claim 1, further including at least one electrode element carried by the support structure operative for emitting energy to ablate tissue, and the method further includes the step of emitting energy to ablate tissue with said at least one electrode element carried by the support structure.

5. The method of claim 1, further including a hemostatic valve located within the catheter body, and the method further includes the step of preventing the flow of fluid into the catheter body with the hemostatic valve.

6. A method of using a probe assembly within a heart, the comprising the steps of:

providing a probe assembly having a catheter body with a distal end, an operative element integrally attached to the catheter body and extending distally beyond the distal end of the catheter body, a support structure integrally attached to the catheter body and extending distally beyond the distal end about an axis for contacting surrounding tissue in the heart, and a steering element integrally carried by the catheter body and connected to the operative element for moving the operative element with respect to the support structure, introducing the catheter body, operative element and support structure together as an integrated assembly into and advancing it through a patient's vasculature with the support element collapsed about the operative element, bringing the support structure into contact with heart tissue by expanding the support structure about the operative element, operating the steering element to move the operative element into a desired position relative to heart tissue while maintaining contact between the support structure and the heart tissue, performing an operative step with the operative element, completely collapsing the support structure about the operative element, and withdrawing the integrated probe assembly from the patient vasculature while the support structure is completely collapsed about the operative element.

7. The method of claim 6, wherein the operative element is adapted to move in a first direction along the axis of the support structure, in a second direction rotating about the axis of the support structure, and in a third direction normal to the axis of the support structure, and the method further includes the step of moving the operative element in at least the three directions.

8. The method of claim 7, further including at least one electrode element carried by the support structure operative for sensing electrical activity in the tissue, and the method further includes the step of sensing electrical activity in the tissue with said at least one electrode element carried by the support structure.

9. The method of claim 7, further including at least one electrode element carried by the support structure operative for emitting energy to ablate tissue, and the method further includes the step of emitting energy to ablate tissue with said at least one electrode element carried by the support structure.

10. The method of claim 7, further including a hemostatic valve located within the catheter body, and the method further includes the step of preventing the flow of fluid into the catheter body with the hemostatic valve.

* * * * *